US009113949B2

(12) United States Patent
Nelson

(10) Patent No.: US 9,113,949 B2
(45) Date of Patent: Aug. 25, 2015

(54) CANNULA SYSTEM AND METHOD FOR IMMOBILIZING AN IMPLANTED CATHETER DURING CATHETER ANCHORING

(75) Inventor: Brian D. Nelson, Birchwood, MN (US)

(73) Assignee: Medtronic, Inc., Minneapolis, MN (US)

( * ) Notice: Subject to any disclaimer, the term of this patent is extended or adjusted under 35 U.S.C. 154(b) by 820 days.

(21) Appl. No.: 13/247,149

(22) Filed: Sep. 28, 2011

(65) Prior Publication Data

US 2012/0083742 A1 Apr. 5, 2012

Related U.S. Application Data

(60) Provisional application No. 61/389,910, filed on Oct. 5, 2010.

(51) Int. Cl.
*A61B 17/34* (2006.01)
*A61B 19/00* (2006.01)

(52) U.S. Cl.
CPC ........... *A61B 17/3403* (2013.01); *A61B 19/201* (2013.01); *A61B 17/3415* (2013.01); *A61B 2017/347* (2013.01); *A61B 2017/3407* (2013.01)

(58) Field of Classification Search
CPC ........... A61B 17/3403; A61B 17/3415; A61B 17/347; A61B 19/201; A61B 19/203; A61B 2017/3405; A61B 2017/3407; A61B 2013/3411; A61B 2017/347; A61M 25/0606; A61M 2025/0175; A61M 2025/024; A61M 2025/0681; A61M 2025/09125
USPC ...................... 604/174, 175, 178, 180, 288.04
See application file for complete search history.

(56) References Cited

U.S. PATENT DOCUMENTS

| | | | |
|---|---|---|---|
| 3,822,697 A | 7/1974 | Komiya | |
| 3,853,127 A | 12/1974 | Spademan | |
| 4,243,034 A * | 1/1981 | Brandt | 604/167.01 |
| 4,311,137 A | 1/1982 | Gerard | |
| 4,449,527 A * | 5/1984 | Hinton | 128/207.17 |
| 4,516,968 A * | 5/1985 | Marshall et al. | 604/174 |
| 4,518,145 A * | 5/1985 | Keltz et al. | 251/5 |
| 5,030,205 A | 7/1991 | Holdaway et al. | |
| 5,126,090 A | 6/1992 | Egolf et al. | |

(Continued)

FOREIGN PATENT DOCUMENTS

WO    WO 2009/061825 A1    5/2009

OTHER PUBLICATIONS

"CRW Precision Arc Stereotactic System" datasheet. Integra NeuroSciences, Integra LifeSciences Corporation, Plainsboro, NJ, 2009; 12 pages.

(Continued)

*Primary Examiner* — Kami A Bosworth
(74) *Attorney, Agent, or Firm* — Mueting, Raasch & Gebhardt, P.A.

(57) ABSTRACT

Devices, systems, and methods for immobilizing an implanted catheter tip while the catheter is anchored relative to surrounding tissue. In one embodiment, a cannula system is included that incorporates a cinch tube for guiding the catheter to a target site within a body. The cinch tube may define a cinch window to receive therein a cinch member operable to immobilize and occlude the catheter. The cinch tube may also include an elongate opening proximate the cinch window. The elongate opening allows extraction of a portion of the catheter and subsequent severing of the catheter above the cinch window/occlusion site.

8 Claims, 20 Drawing Sheets

(56) References Cited

U.S. PATENT DOCUMENTS

| | | | | |
|---|---|---|---|---|
| 5,158,569 | A | * | 10/1992 | Strickland et al. ............ 604/533 |
| 5,183,465 | A | * | 2/1993 | Xanthakos et al. ............ 604/108 |
| 5,368,573 | A | * | 11/1994 | Andrew ........................ 604/158 |
| 5,603,703 | A | | 2/1997 | Elsberry et al. |
| 5,989,223 | A | * | 11/1999 | Chu et al. .................. 604/167.05 |
| 6,591,472 | B1 | | 7/2003 | Noone et al. |
| 7,730,628 | B2 | | 6/2010 | Hoffman |
| 7,879,045 | B2 | * | 2/2011 | Gielen et al. .................. 606/130 |
| 2005/0256455 | A1 | * | 11/2005 | Weststrate et al. ............ 604/104 |
| 2006/0122628 | A1 | * | 6/2006 | Solar et al. .................... 606/130 |
| 2007/0066977 | A1 | | 3/2007 | Assell et al. |
| 2008/0161719 | A1 | * | 7/2008 | Miller et al. .................. 600/567 |
| 2008/0275466 | A1 | | 11/2008 | Skakoon |
| 2009/0143764 | A1 | | 6/2009 | Nelson |
| 2009/0187149 | A1 | | 7/2009 | Nelson |
| 2010/0030184 | A1 | * | 2/2010 | Boulis et al. .................. 604/500 |
| 2011/0009879 | A1 | * | 1/2011 | Derrick et al. ................ 606/130 |
| 2011/0040304 | A1 | * | 2/2011 | Li et al. ........................ 606/130 |

OTHER PUBLICATIONS

U.S. Appl. No. 61/389,910, filed Oct. 5, 2010, Nelson.
U.S. Appl. No. 13/247,203, filed Sep. 28, 2011, Nelson.
"Leksell Stereotactic System® overview" datasheet. Elekta AB, Stockholm, Sweden, Sep. 2010; 22 pages.
"microTargeting™ STar™ Drive System, Directions for Use," datasheet. FHC, Inc., Bowdoin, ME, Rev. C0, Oct. 2010; 49 pages.
"Micro Serrefines" datasheet [online]. Fine Science Tools, Foster City, CA, [retrieved on Dec. 30, 2011]. Retrieved from the Internet:<URL: http://www.finescience.com/Special-Pages/Products.aspx?ProductId=272; 1 page.
"Schwartz Micro Serrefines" datasheet [online]. Fine Science Tools, Foster City, CA, [retrieved on Dec. 30, 2011]. Retrieved from the Internet:<URL: http://www.finescience.com/Special-Pages/Products.aspx?ProductId=278&CategoryId=82>; 1 page.
Final Office Action dated May 15, 2013 in U.S. Appl. No. 13/247,203, 9 pages.
Appeal Brief dated Oct. 15, 2013 in U.S. Appl. No. 13/247,203, 21 pages.
Examiner's Answer dated Nov. 19, 2013 in U.S. Appl. No. 13/247,203, 14 pages.
Reply Brief dated Jan. 14, 2014 in U.S. Appl. No. 13/247,203, 11 pages.

* cited by examiner

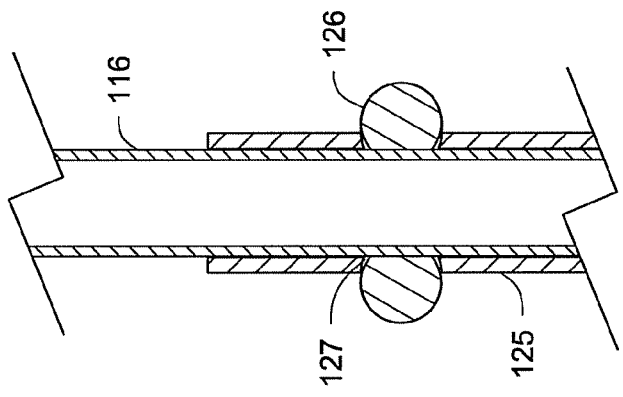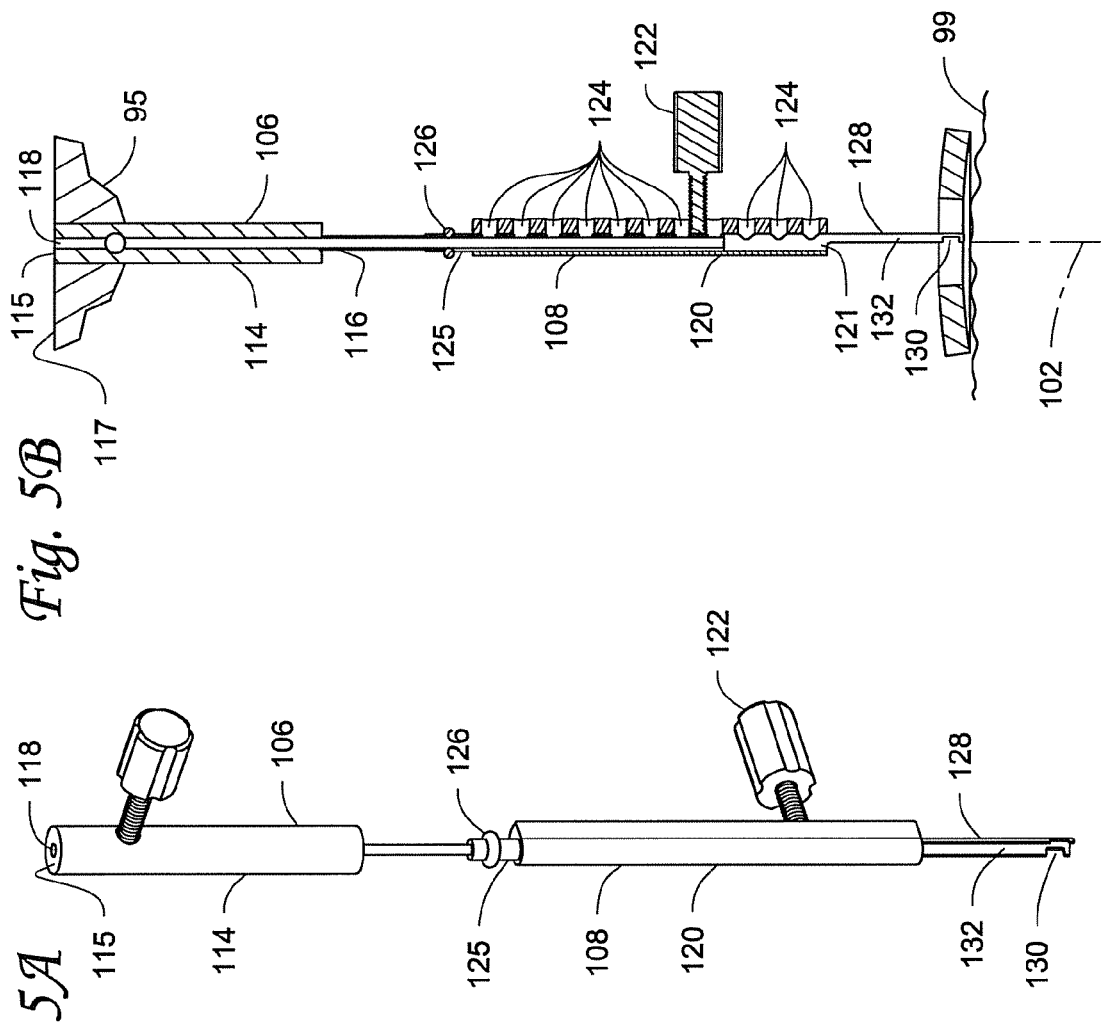

CANNULA SYSTEM AND METHOD FOR IMMOBILIZING AN IMPLANTED CATHETER DURING CATHETER ANCHORING

RELATED APPLICATION(S)

This application claims the benefit of U.S. Provisional Application No. 61/389,910, filed Oct. 5, 2010, the content of which is incorporated herein by reference in its entirety.

TECHNICAL FIELD

Embodiments of the present invention relate generally to medical devices and, more particularly, to cannula systems and methods for immobilizing or restraining a catheter, e.g., brain infusion catheter, while the catheter is being anchored relative to surrounding tissue.

BACKGROUND

Use of a catheter to deliver a therapeutic agent to the brain (e.g., into the intracerebroventricular (ICV), intrathecal, or intraparenchymal (IPA) space) generally involves the insertion of the catheter into the cranial cavity via a burr hole. The catheter may be inserted until a therapy delivering catheter tip is positioned at a predetermined target site, after which the therapeutic agent may be dispensed through the catheter in accordance with a desired therapy profile.

During a typical implantation procedure, an incision is made in the scalp to expose the patient's skull. After forming the burr hole through the skull, the catheter may be inserted into the brain. To accurately place the catheter, surgeons may use stereotactic apparatus/procedures in a process referred to as framed stereotaxy. In framed stereotaxy, a ring-like frame is mounted to the patient's skull by pins or screws. The ring-like frame is then used to determine a three-dimensional data set, from which coordinates for the target site may be calculated. Various components and instruments may be utilized with the stereotactic apparatus to assist in guiding the catheter tip to the target site.

Once the catheter tip is implanted at the target site, an opposite or protruding portion of the catheter (i.e., that portion that remains outside of the skull) may be anchored relative to the burr hole, e.g., via a burr hole anchor surgically attached to the skull. An end of the protruding portion of the catheter may then be connected, often via a secondary catheter, to a reservoir containing the therapeutic agent. After the secondary catheter is connected and tunneled beneath the skin to the reservoir, the scalp incision(s) may be closed and the system may deliver therapy in accordance with the desired profile.

As one can appreciate, implantation of a catheter within the brain, via framed stereotaxy procedures or otherwise, may present problems. For instance, the process of physically attaching the catheter to the burr hole anchor may inadvertently impart loads to the catheter that are capable of displacing the catheter tip relative to the target site. Depending on the application, even slight displacement of the tip may result in reduced therapeutic efficacy.

Moreover, for some therapeutic agents, e.g., those of higher molecular weight, delivery to the brain may be hampered by fluid pressure within the brain. In some instances, this fluid pressure may allow blood to enter the catheter tip and travel upwardly into the catheter. To address this issue, the reservoir may be configured as a pressurized infusion pump to provide convection enhanced delivery (CED) of the therapeutic agent.

While CED may address some instances of reverse fluid flow during drug infusion, blood entry into the catheter tip may still occur, e.g., after the catheter is implanted but before it is connected to the infusion pump. Depending on the catheter construction and the time period between implantation and the start of infusion, any blood that has entered the catheter may ultimately clot, potentially interfering with, or even blocking, subsequent delivery of the therapeutic agent.

SUMMARY

The present invention may overcome these and other issues with prior devices, systems, and methods by, in one embodiment, providing a cannula system for immobilizing a device within a mammalian body while the device is anchored to surrounding tissue. The system may include a guide tube having a body fixable to a surgical apparatus, and an elongate cinch tube having an outer surface and an inner surface, wherein the cinch tube is configured to slidably engage the guide tube. A cinch member may also be provided and include a clamp element configured to engage the cinch tube and immobilize the device relative to the cinch tube when the device is positioned within the cinch tube.

In another embodiment, a cannula system is provided. The system may immobilize a tip of a catheter relative to a target site located within a mammalian skull while the catheter is being secured relative to a burr hole aligned with the target site. The system includes a guide tube having: a body fixable relative to a surgical apparatus located outside of the burr hole, and an elongate tubular extension protruding from the body of the guide tube towards the target site. The system further includes an elongate cinch tube having an inner surface and an outer surface, the inner surface configured to slidably receive the extension therein, wherein a cinch window is formed between the inner and outer surfaces near a distal end of the cinch tube. A catheter is provided and configured for insertion through both the guide tube and the cinch tube. A cinch member having a first clamp element configured to pass through the cinch window and compress the catheter against the inner surface of the cinch tube is also included.

In yet another embodiment, a method of implanting a therapy delivery catheter and immobilizing the catheter while the catheter is coupled to an infusion source is provided. The method includes: implanting the catheter such that a distal tip of the catheter is located at a predetermined target site, wherein the catheter is at least partially supported by a cinch tube; and applying a clamping member to the catheter at a cinch location associated with the cinch tube, wherein the clamping member is configured to both occlude a lumen defined by the catheter, and restrain the catheter relative to the cinch tube at the cinch location. The method also includes: severing the catheter at a cut location between the cinch location and a proximal end of the catheter; connecting the catheter to the infusion source; and removing the clamping member.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein:

FIGS. 5A-5C illustrate an exemplary embodiment of an assembled guide tube and cinch tube of the cannula system of FIGS. 3 and 4, wherein: FIG. 5A is a perspective view; FIG. 5B is a section view; and FIG. 5C is an enlarged view of a portion of FIG. 5B;

FIGS. 6A-6B illustrate an exemplary cannula system with a guide cannula inserted into the guide tube and cinch tube, wherein FIG. 6A is a perspective view also illustrating an obturator; and FIG. 6B is a section view;

FIGS. 10A-10B illustrate exemplary retainers in accordance with embodiments of the instant invention, wherein: FIG. 10A is a perspective view of the retainer of FIG. 9; and FIG. 10B is an exploded perspective view of an alternative embodiment of the retainer;

FIGS. 16A-16B illustrate the burr hole anchor and cinch tube after the catheter has been fluidly coupled to a delivery catheter, wherein: FIG. 16A is a perspective view; and FIG. 16B is section view.

Figure 1:
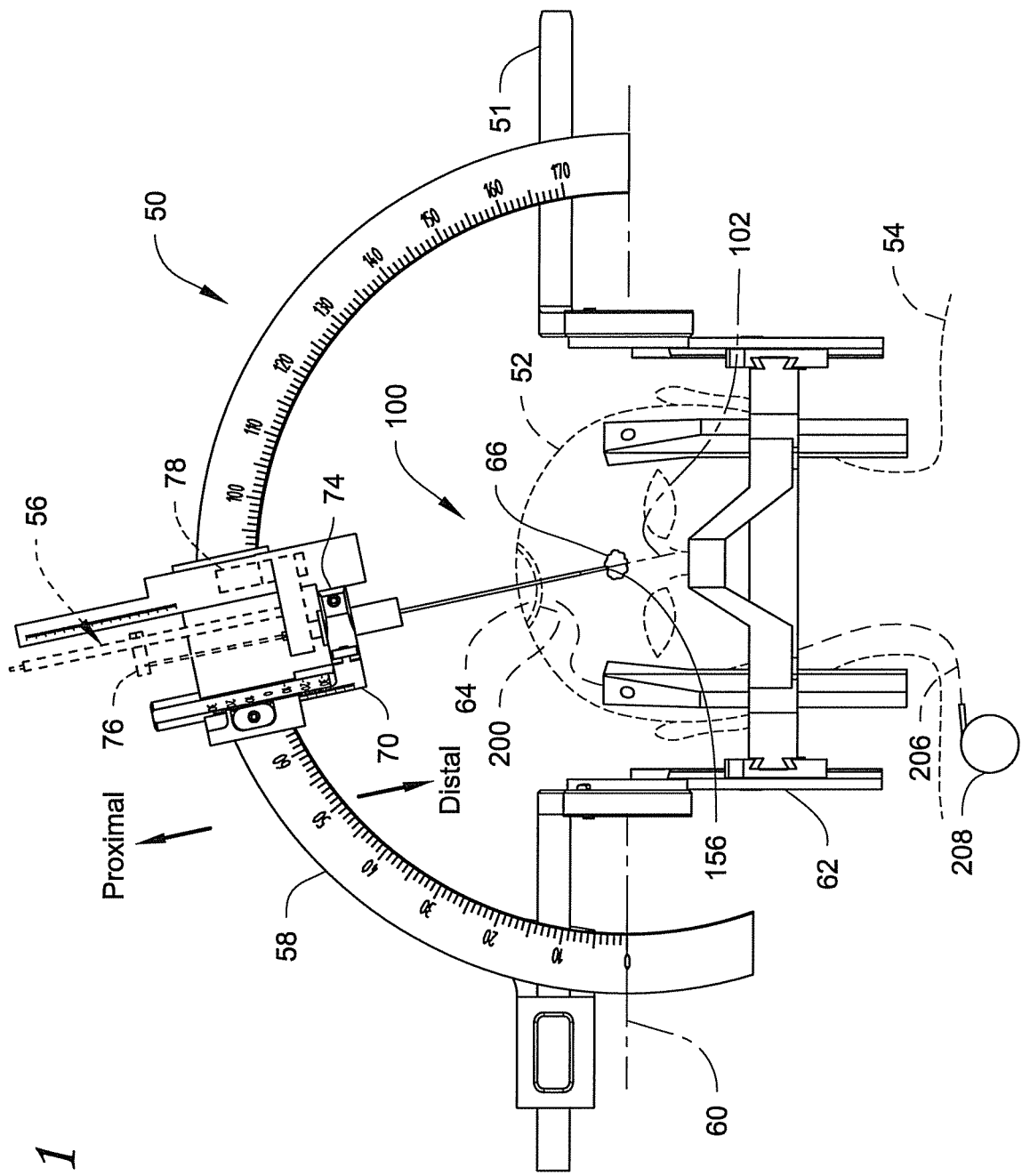
FIG. 1 is a diagrammatic perspective view of an exemplary cannula system in accordance with embodiments of the invention, the system shown in conjunction with a stereotactic frame attached to a patient's head.

The figures are rendered primarily for clarity and, as a result, are not necessarily drawn to scale. Moreover, various structure/components, including but not limited to fasteners, bearings, electrical components (wiring, cables, etc.), fluid components, and the like, may be shown diagrammatically or removed from some or all of the views to better illustrate aspects of the depicted embodiments, or where inclusion of such structure/components is not necessary to an understanding of the various exemplary embodiments of the invention. The lack of illustration/description of such structure/components in a particular figure is, however, not to be interpreted as limiting the scope of the invention in any way.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

Embodiments of the instant invention may be directed to medical systems and devices, as well as to procedures for using the same. For instance, one embodiment of the invention is directed to a cannula system for implanting and/or positioning a tip of a medical device, e.g., a catheter, in three-dimensional space within a human or other mammalian body, and immobilizing the device while it is being anchored relative to surrounding tissue (e.g., bone). In the illustrated embodiment, exemplary systems and methods are described and illustrated in the context of implanting a tip of a brain therapy catheter into brain tissue within a skull cavity, e.g., through a burr hole formed in skull tissue (e.g., of a human or other mammalian body). The system may then be used to immobilize the catheter, i.e., the catheter tip, while the catheter is: secured to a burr hole anchor surrounding the burr hole; and connected to a therapy source such as an implantable infusion pump. However, this is not limiting as implantation of other devices, and implantation through other portals, are contemplated without departing from the scope of the invention.

FIG. 1 illustrates a cannula system 100 in accordance with one embodiment of the present invention. As illustrated in this view, the system 100 may optionally be utilized with a separate surgical apparatus, e.g., stereotactic system 50, as is known in the art (see, e.g., the Leksell stereotactic system distributed by Elekta AB of Stockholm, Sweden; or the CRW stereotactic system distributed by Integra Radionics, Inc. of Burlington, Mass., USA). The stereotactic system 50 may include a frame 51 fixedly attached to the head or skull 52 of a patient and positioned relative to a burr hole 64 formed through the skull. The cannula system may also optionally include a drive or drive member to which various surgical instruments may be attached. The drive member may be configured to selectively translate an elongate surgical instrument into and out of the skull 52 via the burr hole 64. While illustrated herein as using the stereotactic system 50 and drive member, cannula systems in accordance with embodiments of the present invention may be used without these items, or may be used with other surgical apparatus/placement systems, without departing from the scope of the invention.

An exemplary stereotactic frame 51 may include an arc-shaped guide 58 along which a mount 70 may be adjustably positioned. The arc-shaped guide 58 may move, e.g., pivot about a transverse pivot axis 60, relative to a mounting portion 62 of the frame 51. As a result of this construction, the mount 70 may position and align the surgical instrument to reach most any location in localized three-dimensional space within the skull 52.

During an exemplary surgical procedure, an incision may be made in the scalp and a portal, e.g., the burr hole 64, may be formed within the skull 52. The burr hole 64 may be located based upon a previously determined location of a target site 66 to which therapy is to be administered such that the burr hole (and its associated anchor) is aligned with the target site 66. The approximate location of the target site 66 may be determined based upon various imaging (e.g., CT, MRI) and mapping techniques as are known in the art. A burr hole anchor 200 (see also, e.g., FIG. 11) may be used to secure the instrument (e.g., a therapy delivery device such as a catheter 156 (described in more detail below)) relative to the burr hole 64 after implantation.

As used herein, relative terms such as "left," "right," "fore," "forward," "aft," "rearward," "top," "bottom," "upper," "lower," "above," "below," "horizontal," "vertical," and the like are, unless otherwise stated, from the perspective shown in FIG. 1. These terms are used herein to simplify the description, however, and not to limit the scope of the invention in any way. Similarly, the relative terms "proximal" and "distal" may be used herein to describe various aspects of the components of the system. Where so used, these terms are defined from the perspective of a clinician, i.e., "proximal" indicates a direction or portion of the particular component/system that is positioned (or intended to be positioned) outside or towards the outside of the skull, while "distal" refers to a direction or portion that is at or more near (or intended to be at or more near) the predetermined target site 66.

Once the target site 66 is located and the burr hole 64 is formed, the guide 58 and stationary mount 70 may be adjusted such that the mount 70 is generally aligned with the burr hole and the target site 66. Once so located, the mount 70 may be generally fixed in place, e.g., fixed so as to restrict movement of the mount along the guide 58 and about the axis 60, by fasteners or the like. At this point, the catheter 156 may be delivered, via the burr hole, to the target site 66. In one embodiment, such delivery may occur by manual insertion controlled by the clinician. In alternative embodiments, catheter 156 delivery may be at least partially automated with the use of the optional drive member, e.g., a microdrive 56. An exemplary microdrive 56 may be similar in some respects to a deep brain stimulation (DBS) microdrive, see, e.g., the "microTargeting Drive System for Stereotactic Positioning" distributed by FHC Inc., of Bowdoin, Me., USA. Once again, while portions of the following description make reference to the use of a microdrive 56, such use is optional, i.e., manual catheter insertion methods are clearly within the scope of the invention.

Figure 2:
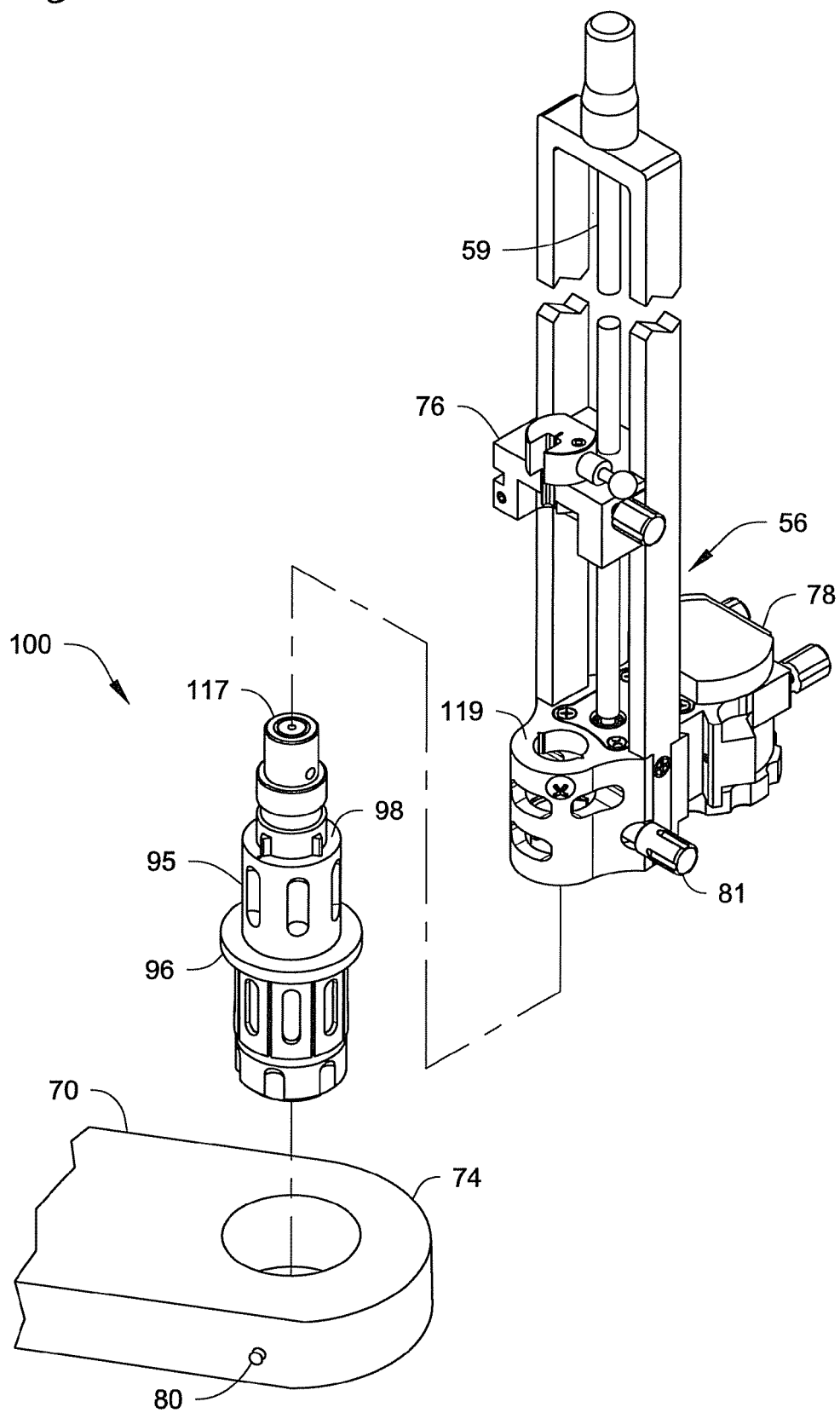
FIG. 2 is a partial exploded perspective view of an exemplary adapter attachable to the stereotactic frame and an optional drive system both for use with cannula systems in accordance with embodiments of the present invention.

In the illustrated embodiment of FIG. 2, the microdrive 56 may be attached to the mount 70 of the stereotactic system 50 with an adapter 95. The adapter 95 may permit attachment of the cannula system to various stereotactic systems (e.g., the Leksell or CRW systems). As illustrated in FIG. 2, the adapter 95 may be placed within an opening formed in a fixed platform 74 of the mount 70 and secured in place, e.g., with a fastener (e.g., a thumb screw 80) or, alternatively, via the adapter incorporating an expandable collet (e.g., a lower portion of the adapter may thread into an upper portion, causing the upper portion to expand within the opening of the platform 74). The adapter 95 may include a flange 96 or other locating feature to index the adapter relative to the fixed platform 74, e.g., the flange 96 may abut an upper surface of the platform when fully seated. In the illustrated embodiment, the adapter 95 may further include a male portion that protrudes upwardly and is received within an opening of the microdrive 56 as indicated in FIG. 2. As with adapter 95 attachment to the platform 74, the microdrive 56 may similarly be secured relative to the adapter with a fastener (e.g., thumbscrew 81). The adapter 95 may include another locating feature, surface 98, against which the microdrive 56 may rest when fully seated.

The adapter 95 may define a frame stop surface 117 that is located a predetermined distance from the platform 74 when the adapter is correctly installed. This surface 117, which may coincide with an associated surface 119 of the microdrive 56 when the latter is utilized, may provide a reference point for subsequent implantation procedures, embodiments of which are further described below.

Once the adapter 95 is accurately affixed to the mount 70, the stereotactic system 50 may define a first portion, e.g., the fixed platform 74 (see, e.g., FIGS. 1 and 2), to receive and hold instruments (as well as a base of the optional microdrive) in a fixed relationship relative to the target site 66.

In configurations incorporating the optional microdrive 56, the system 50 may also define a second portion, e.g., a carrier platform 76 (see also FIG. 3), to also receive and hold various instruments. As further explained herein, the carrier platform 76 may be selectively movable, e.g., translatable along a drive screw 59, relative to the first portion (fixed platform 74) to selectively advance or withdraw an instrument attached to the carrier platform. In the illustrated embodiment, the carrier platform 76 may be advanced or withdrawn by a motor 78 (diagrammatically illustrated in FIGS. 2 and 3).

Figure 3:
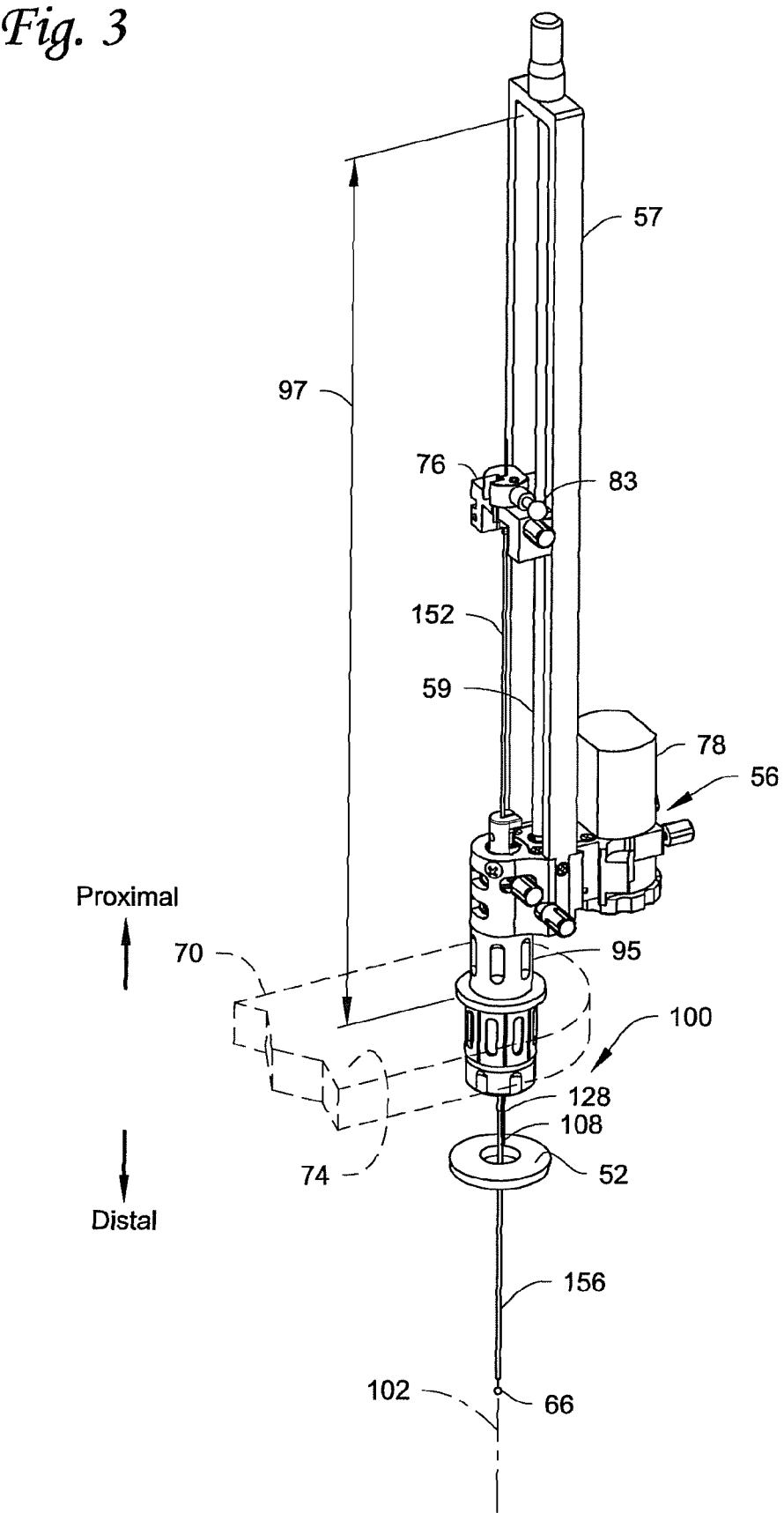
FIG. 3 is an enlarged perspective view of the cannula system of FIG. 1 as utilized with the optional drive system, the cannula system illustrated as it positions a catheter through a burr hole and to a target site (portions of the stereotactic frame removed for clarity from this and subsequent views)

The exemplary cannula system 100 is illustrated in more detail in FIG. 3 (the stereotactic system (e.g., frame 51 and guide 58) may be removed in this and subsequent views for clarity). As shown in FIG. 3, the cannula system 100 may once again include the adapter 95 to permit use of the cannula system with existing stereotactic systems (e.g., the Leksell or CRW systems). The adapter 95 may directly support the cannula system 100 and/or engage and support the optional microdrive 56.

In the embodiment illustrated in FIG. 3, a height 97 of the microdrive 56 may be configured to be about 150 to 500 millimeters or more (e.g., about 390 mm) to accommodate a desired motion of the cannula system 100 (e.g., of the carrier platform 76). That is, heights within such a range may permit the desired motorized motion of the carrier platform 76 as further described below. Of course, the height 97 may vary within, or even be above or below, the identified range to accommodate different implantation applications.

In addition to the elongate powered drive screw 59, the microdrive 56 may include a frame 57 as also shown in FIG. 3. Rotation of the screw 59 (e.g., by the motor 78) may permit translation of the carrier platform 76 (within the confines defined by the frame 57) in either direction along a longitudinal axis 102 of the system 100 (i.e., along the screw). As a result, any portion of the cannula system 100 that is attached to the carrier platform 76 may be displaced accordingly.

Figure 4:
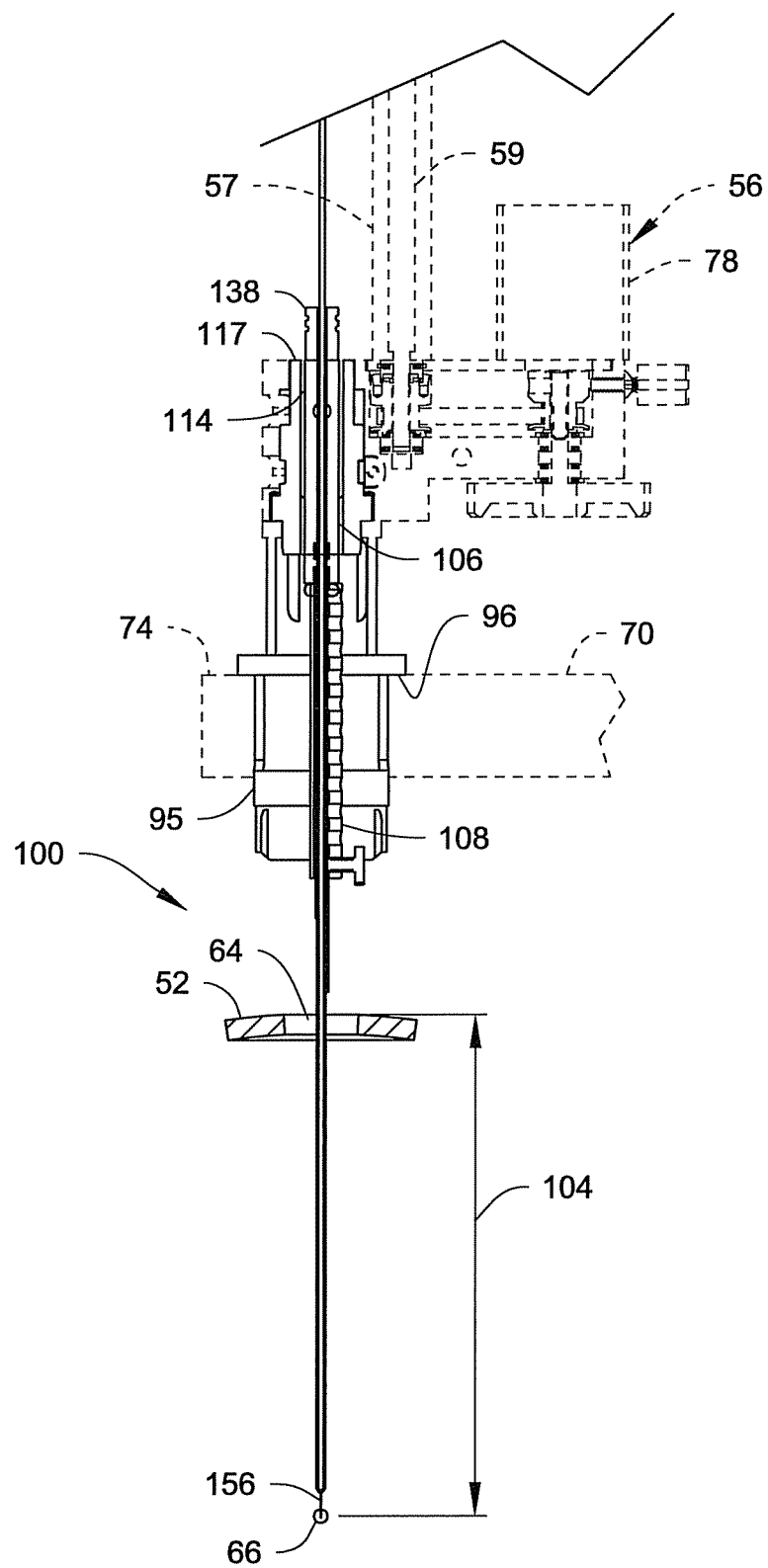
FIG. 4 is a partial section view of the cannula system of FIG. 3 (illustrating the optional drive system in broken lines)

FIG. 4 is a cross sectional view of a portion of the exemplary cannula system 100 in a stereotactic system incorporating the microdrive 56. As shown in this view, the exemplary system 100 may be configured to accommodate a "skull-to-target" distance 104 of about 45 to 95 mm. However, those of skill in the art will again realize that various design parameters could certainly be adjusted to accommodate different skull-to-target distances.

As further shown in FIG. 4, the cannula system 100 may include, among other components, a frame guide tube 106, an elongate cinch tube 108, and a catheter (e.g., the needle tip catheter 156) configured for insertion through both the guide tube and the cinch tube as further described below. A guide cannula 138 may also be included in some embodiments. Each of these components is described in more detail below, as are exemplary methods for using the system 100.

FIGS. 5A-5C illustrate the guide tube 106 assembled with the cinch tube 108, wherein FIG. 5A is a perspective view, FIG. 5B is a section view, and FIG. 5C is an enlarged view of a portion of FIG. 5B. As illustrated in these views, the guide tube 106 may include a body 114 and an elongate tubular extension 116 protruding or extending from the body, e.g., extending towards the target site 66 (see FIG. 4). The body 114, e.g., an outer surface of the body, may be configured to be fixed or securely retained relative to a surgical apparatus located outside the burr hole, e.g., relative to the adapter 95 and thus relative to the fixed platform 74 as illustrated in FIG. 4. Although other configurations are certainly possible, an upper surface 115 the body 114 may be configured to align with the frame stop surface 117, which in the illustrated embodiment, is defined by an upper surface of the adapter 95 (which may also align with the surface 119 of the microdrive 56 as indicated in FIGS. 2, 4, and 5B). As a result, the guide tube 106 may remain fixed relative to the stereotactic system 50 or other external surgical apparatus during the implantation procedure. Moreover, the distance from the frame stop surface 117 to the target site 66, once fixed, may remain constant throughout the implantation procedure.

Notwithstanding this fixed relationship, the cinch tube 108 may be longitudinally displaced relative to the guide tube 106, e.g., along the tubular extension 116 of the guide tube, as is clearly evident in FIG. 5B. Regardless of the relative location of the cinch tube 108, the guide tube 106 and the cinch tube remain aligned with the longitudinal axis 102 (see also FIGS. 1 and 5B) of the cannula system 100 throughout implantation. Stated alternatively, the guide cannula and cinch tube remain generally directed at/aligned with the target site 66 as shown in FIG. 4.

In one embodiment, the guide tube 106 may be formed with the body 114 integral with the tubular extension 116. In alternative embodiments, the tubular extension 116 may be a standard hypodermic needle, e.g., a 14 gage RW 316 stainless steel needle, which is welded or otherwise attached to the body 114. Regardless of the construction of the guide tube, it may define a passageway or lumen 118 passing completely through the body 114 and the extension 116 as shown in FIG. 5B.

The cinch tube 108 may, similar to the guide tube 106, define a tubular body 120 and have an outer surface, an inner surface, and a lumen 121 passing through the cinch tube from end to end. The cinch tube 108 may be configured to slidably engage the guide tube 106. For example, as shown in the figures, the inner surface (e.g., lumen 121) of the cinch tube 108, e.g., a tubular protrusion 125 of the cinch tube, may slidably receive the extension 116 of the guide tube therein. The tubular protrusion 125 may, in one embodiment, be a hypodermic needle that is welded or press fit into the lumen 121 such that it protrudes from the body 120 and towards the guide tube 106 (e.g., upwardly in the figures).

The body 120 of the cinch tube 108 may include a retaining or lock member, e.g., threaded fastener 122, operable to secure and lock the cinch tube relative to the guide tube 106 at one or more longitudinal locations along the tubular extension 116 of the guide tube.

To accommodate the fastener 122, the body 120 of the cinch tube 108 may define at least one threaded receiver location, e.g., threaded aperture 124, passing completely through a wall of the cinch tube. Each threaded aperture 124 may be configured so that the fastener 122 may threadably engage the cinch tube 108 to selectively lock the guide tube relative to the cinch tube. In the illustrated embodiment, the body 120 of the cinch tube includes a plurality of threaded apertures 124 each operable to threadably receive the fastener 122. Thus, as shown in FIG. 5B, the fastener 122 may thread into one of the apertures 124 through the wall of the cinch tube 108 where it may then contact and press against the tubular extension 116 of the guide tube. When tightened, the fastener 122 applies a force sufficient to hold the cinch tube 108 in the desired location relative to the guide tube 106. By loosening the fastener 122, the cinch tube 108 may be relocated longitudinally along the guide tube 106, where it may be retightened upon reaching the desired position. Preferably, the tubular protrusion 125 is configured so as not to interfere with passage of the fastener 122 through the various apertures 124.

To ensure a minimal amount of friction between the guide tube 106 and the cinch tube 108 when the fastener 122 is loosened, a friction member may be provided, e.g., between the guide tube and the cinch tube. In the illustrated embodiment, the friction member is configured as an O-ring 126 positioned within one or more channels or windows 127 formed in the tubular protrusion 125 of the cinch tube 108 as shown in FIG. 5C. The windows 127 pass completely through the tubular protrusion 125 such that the O-ring 126 may surround the tubular protrusion, yet extend inwardly through the window to contact the tubular extension 116 of the guide tube 106. The windows 127 and O-ring 124 are sized to ensure that the O-ring presses sufficiently against the tubular extension 116 of the guide tube 106 when the cinch tube 108 and guide tube are assembled. The inclusion of the friction member may reduce the occurrence of unintended relative movement of the cinch tube 108 (e.g., the cinch tube sliding or "falling" into the burr hole) when the fastener 122 is loosened.

The cinch tube 108 may also include a tubular extension 128 extending from the body 120 towards the target site 66 as shown in FIGS. 5A-5B. Similar to the construction of the guide tube 106, the extension 128 may be formed integrally with the body 120 of the cinch tube 108, or it may be formed from a modified hypodermic needle affixed, e.g., welded, to the body 120. In one embodiment, the extension 128 may be constructed of 12 gage RW 316 stainless steel hypodermic tubing. However, other materials and constructions are certainly possible without departing from the scope of the invention.

Unlike the tubular extension 116 of the guide tube 106, the tubular extension 128 may define a window, e.g., cinch location or cinch window 130, passing completely through the wall of the extension (between the outer surface and the inner surface). In the illustrated embodiment, the cinch window 130 is located near a distal end of the cinch tube, but other embodiments may place the cinch window at most any location.

The extension 128 may further define an elongate opening 132 formed between the outer surface and the inner surface of the cinch tube along a longitudinal section. In one embodiment, the elongate opening is located proximate the cinch window 130. In the illustrated embodiment, the elongate opening 132 runs generally the entire length of the extension 128, yielding a tubular extension 128 that is generally C-shaped or U-shaped in cross section. The elongate opening 132 may, in the illustrated embodiments, be located on an opposite side of the cinch tube from the apertures 124 (although such a configuration is not limiting). While shown as extending substantially the entire longitudinal length of the extension, the opening 132 may, in other embodiments, extend over only a portion of the longitudinal length. In one embodiment, the window 130 and elongate opening 132 are formed by milling or by wire electron discharge machining of a hypodermic tube that is welded to the body 120. The purpose of the cinch window 130 and the elongate opening 132 is described in more detail below.

With this description of an exemplary embodiment of the guide tube 106 and cinch tube 108, exemplary methods for implanting a medical device, e.g., a catheter, through a burr hole and immobilizing the device during subsequent anchoring, will now be described with reference primarily to FIGS. 6A-17. Where beneficial, other mechanical/structural aspects and components of various embodiments of the cannula system 100 will be described in the context of the exemplary methods.

Figure 6A:
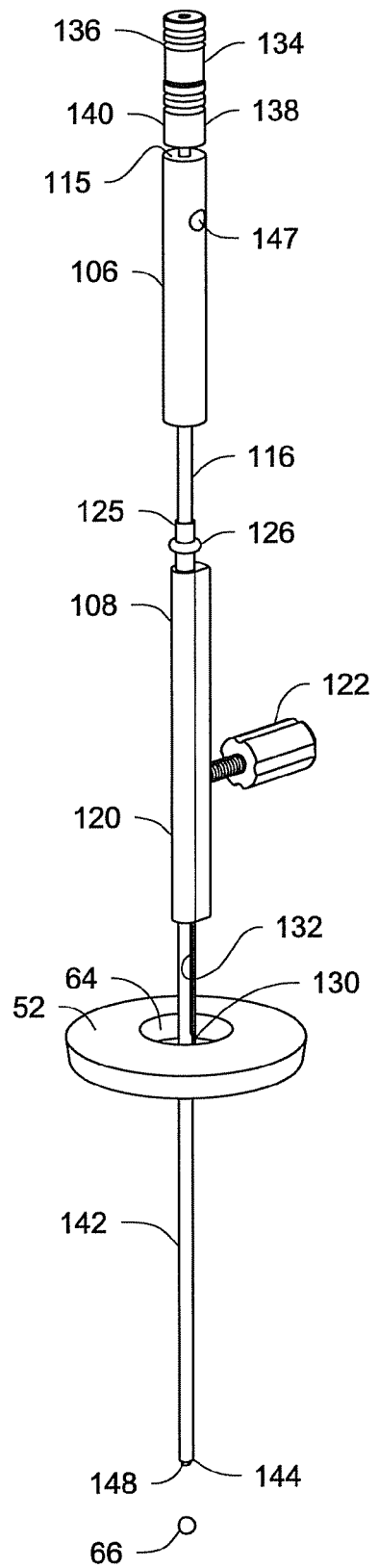
Figure 6B:
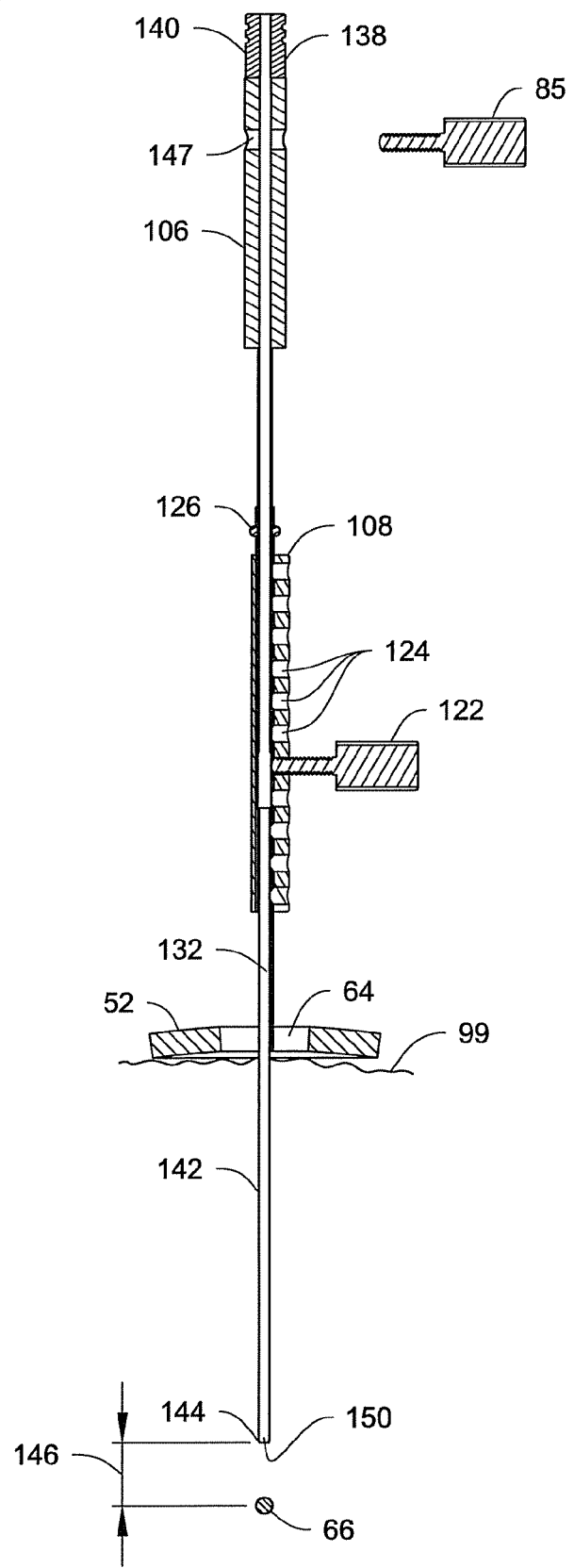

FIGS. 6A and 6B illustrate the exemplary cannula system 100 after formation of the burr hole 64 through the skull 52. These and subsequent figures represent a surgical configuration after the stereotactic system 50 (see FIG. 1) is in place and the guide tube 106 has been secured within the adapter 95 and the fixed platform 74 (see FIG. 4). To better illustrate the cannula system 100, some structure, e.g., the stereotactic system 50, the adapter 95, and the anchor 200 (see FIG. 11), may be removed from these and some of the subsequent views.

The cinch tube 108 may first be lowered along the tubular extension 116 of the guide tube 106 until the cinch window 130 (see FIGS. 5A-5B) is just above the dura 99. The cinch tube 108 may be lowered by loosening the fastener 122 and moving the cinch tube to the desired location. Once again, the O-ring 126 may prevent unintended sliding of the cinch tube 108 towards the dura when the fastener is loosened. By providing numerous threaded apertures 124 (see FIG. 5B), the fastener 122 may be located within an aperture that allows the fastener to engage the tubular extension 116 of the guide tube, e.g., as the cinch tube 108 is moved downwardly, use of a higher aperture 124 may be required to ensure fastener contact with the tubular extension 116 of the guide tube.

Figure 7:
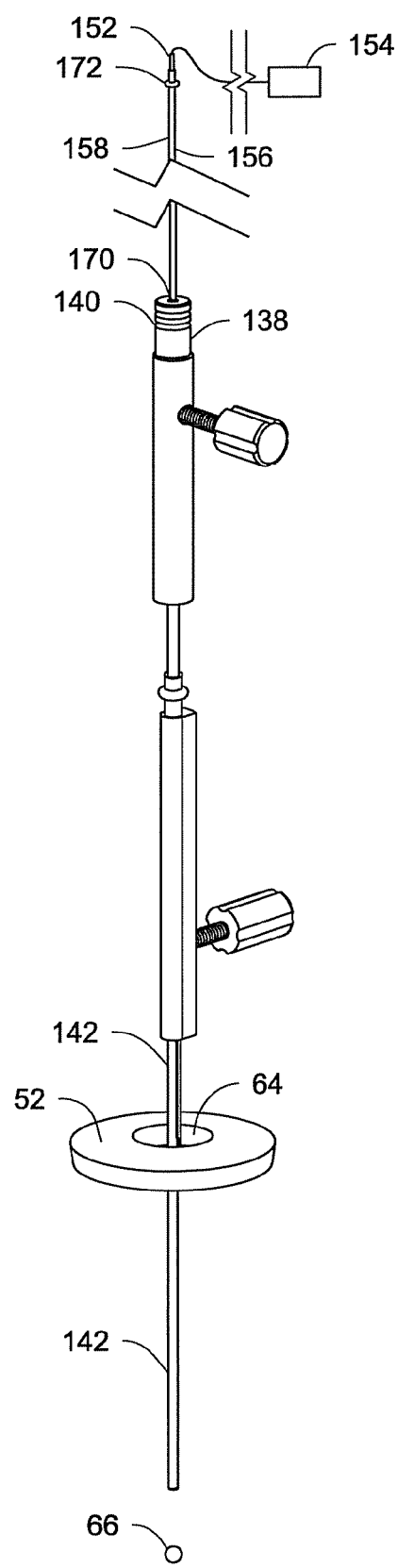
FIG. 7 illustrates the cannula system of FIGS. 6A-6B with the obturator removed and a catheter and an infusing stylet inserted into the guide cannula.

While not illustrated in FIGS. 6A, 6B, and 7, a burr hole anchor may be attached to the skull at the burr hole 64 prior to the positioning of the cinch tube 108. While a variety of burr hole anchor configurations are suitable, the anchor may, in one embodiment, be configured in accordance with embodiments shown and described in U.S. patent application Ser. No. 12/357,120 (U.S. Pat. App. Pub. No. 2009-0187149-A1), incorporated herein by reference in its entirety. Such an exemplary embodiment is represented as anchor 200 herein in FIGS. 11-17.

When using an anchor such as the anchor 200, the cinch window 130 and elongate opening 132 (see FIG. 5A) may be oriented to align with cinch points located on the anchor as further described below. Moreover, the fluid delivery conduits within and upstream of the anchor (e.g., internal anchor plumbing and a source or delivery catheter 206 (see, e.g., FIG. 1)) may be primed, e.g., with an implantable infusion pump or a syringe pump before or during the implantation procedure.

As shown in FIG. 6A, an obturator 134 having a flange or head 136 may be inserted into a guide cannula 138. The guide cannula 138 may also include a flange or head 140 and a tubular body 142. The guide cannula 138 may also define a lumen or passageway 150 (see also FIGS. 6B and 8) passing completely through the cannula (e.g., through the head and tubular body). The tubular body 142 of the guide cannula 138 may have a body length selected to place its inserted tip 144 at a preset distance 146 from the target site 66 as shown in FIG. 6B. In the illustrated embodiment, this body length corresponds to the fixed distance measured from the upper surface 115 of the guide tube 106 (which, as shown in FIG. 5B, is aligned with the frame stop surface 117) to the target site 66, minus the preset distance 146. In one embodiment, the preset distance 146 is about 10 mm, but other distances are certainly possible without departing from the scope of the invention.

The obturator 134 may include a blunt, rounded tip 148 that protrudes just beyond the distal tip 144 of the body 142 of the guide cannula 138 when the head 136 of the obturator is flush against the head 140 of the guide cannula as shown in FIG. 6A. As a result, the guide cannula/obturator may be manually inserted into the proximal end of the guide tube 106 as also illustrated in FIG. 6A. As the assembly 134/138 is pushed downwardly, the obturator/guide cannula may penetrate the brain tissue. The obturator may assist with cannula penetration while reducing or avoiding brain tissue damage (coring). When the head 140 of the guide cannula contacts the upper surface 115 of the guide tube 106, the tips 144 and 148 may be located at the desired preset distance 146 from the target site 66.

Once the guide cannula 138 is fully inserted (e.g., when the head 140 rests against the surface 115), the guide cannula may be secured in place to the stereotactic frame (e.g., with a thumb screw 85 or the like passing through an opening 147 in the guide tube 106). The obturator 134 may then be manually withdrawn (lifted upwardly in FIG. 6A) and removed, leaving the guide cannula 138 in the position shown in FIGS. 6B and 7.

With the obturator removed, one end of a hollow tubular stylet 152 may be connected to a pressurized infusion source 154 such as a syringe pump (e.g., a model PHD 2000 Harvard Apparatus pump distributed by Instech Laboratories, Inc. of Plymouth Meeting, Pa., USA) as shown in FIG. 7 to prime and maintain a constant infusing flow of fluid, e.g., phosphate buffered saline (PBS) fluid, through the stylet. An opposite or distal end of the stylet may then be inserted into a proximal end of a catheter, e.g., the needle tip catheter 156. While the flow rate through the stylet 152 may vary, it is, in one embodiment, maintained at about 2 to about 10 micro liters/minute ($\mu$l/min), e.g., about 5 ml/min.

Figure 8:
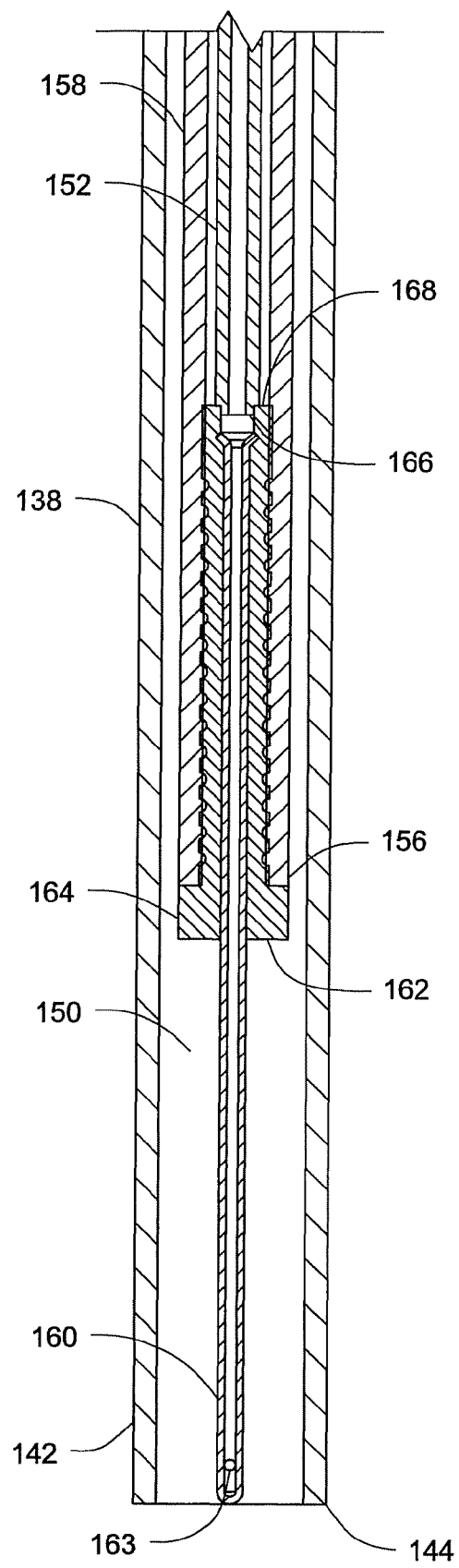
FIG. 8 is an enlarged section view of a therapy delivering end of the exemplary catheter of FIG. 7 after insertion of the catheter and stylet into the guide cannula.

The needle tip catheter 156 may, in one embodiment, be configured in accordance with embodiments described and illustrated in U.S. patent application Ser. No. 12/276,794 (U.S. Pat. App. Pub. No. 2009-0143764-A1), incorporated herein by reference in its entirety. The catheter 156 may thus include a flexible (e.g., urethane) body 158 and a rigid needle tip 160 as shown in FIG. 8. A ledge 162 may also be formed at the transition between the needle tip and the body. The ledge 162 may provide various benefits including, for example, reduced backflow of therapeutic substance along the catheter length. The ledge may, in one embodiment, be formed by an insert 164 fixed within the distal end of the body 158. While various embodiments are possible, the needle tip 160 may be configured as a closed tip with one or more side flow openings 163 in communication with a lumen of the catheter.

The infusing stylet 152 may be manually inserted into the catheter 156 until a tip 166 of the stylet abuts an inner contact surface 168 formed in the catheter, e.g., a surface of the insert 164. The stylet 152 may be sufficiently rigid to permit pushing of the catheter 156 into the guide cannula 138 by application of a force to the stylet at its upper or proximal end, thereby allowing positioning of the tip of the catheter. Accordingly, the assembled stylet and catheter may be manually inserted into the guide cannula 138 (which is itself inserted through both the guide tube and cinch tube) until the tip of the catheter 156 is generally at the same location as an opening at the tip 144 of the guide cannula 138 as shown in FIG. 8. The catheter may include indicia, e.g., a mark 170, along its length that aligns with an upper surface of the head 140 of the guide cannula 138 when the catheter is fully inserted (as shown in FIG. 7, the catheter and stylet may both protrude outwardly beyond (e.g., above) the head 140 of the guide cannula when the catheter is fully inserted).

In the illustrated embodiment, infusing of the stylet 152 may continue as the stylet and catheter are inserted through the guide cannula 138. This may ensure that a continuous positive flow of PBS fluid out the tip (e.g., from the side flow openings 163) of the catheter is maintained during catheter positioning. During this process, some PBS fluid may escape at the interface between the tip 166 of the stylet and the contact surface 168 of the catheter 156 (see, e.g., FIG. 8). To prevent this fluid from leaking upwardly through the annular region between the catheter and the stylet, a constricting, e.g., sealing, member may be provided near the upper (proximal) end of the catheter. In the illustrated embodiment, the sealing member may be configured as an O-ring 172 as shown in FIG. 7 that is placed around the catheter body to compress and seal the generally elastic catheter body 158 against the more rigid outer surface of the stylet 152. By accurate sizing of the O-ring 172, a sufficient radial sealing force may be provided that reduces or eliminates fluid leakage out of the annular space between the catheter and the stylet.

By continuing to infuse the stylet 152 (and accompanying catheter 156), a constant positive pressure (and thus positive flow) through the catheter may be maintained during implantation, potentially preventing blood from entering the catheter via the side flow openings 163. While such a configuration provides potential benefits, the infusion source 154, corresponding infusing flow, and the O-ring may be eliminated in other applications without departing from the scope of the invention.

With the catheter 156 located as shown in FIG. 8, the stylet 152 may be displaced downwardly into the tissue (e.g., towards the target 66). In one embodiment, this displacement of the stylet and catheter may be achieved by attaching the stylet to the microdrive 56, e.g., to the motorized carrier platform 76 (see FIG. 3), using a thumb screw 83 or other stylet holder (including devices such as those described in U.S. patent application Ser. No. 13/247,203, entitled Retainer for Immobilizing an Implanted Catheter during Stylet Retraction, and Stylet Holder for Use with Same, filed on same date herewith, the disclosure of which is incorporated herein by reference in its entirety). The clinician may then actuate the motor 78 to drive the stylet 152 and catheter 156 downwardly the predetermined distance 146 (see FIG. 6B) at a controlled rate. In one embodiment, the descent rate is about one mm/minute, although other rates are certainly possible. Alternatively, the stylet may be manually displaced by the clinician.

Figure 9:
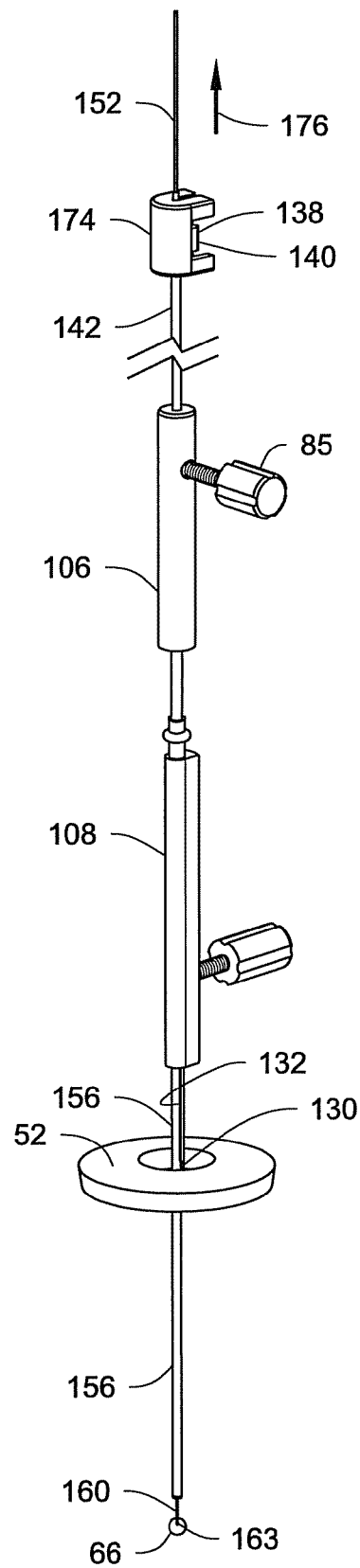
FIG. 9 is a perspective view of the cannula system after partial retraction of the guide cannula and during retraction of the stylet, wherein a retainer in accordance with one embodiment of the invention is shown holding the catheter in place during stylet extraction.

Once the stylet 152 and catheter 156 have descended by a distance equal to the present distance 146, the tip (e.g., side flow opening 163) of the catheter 156 may be positioned at the target site 66 as shown in FIG. 9.

At this point, the guide cannula 138 may be manually raised (while holding the stylet 152 and catheter 156 stationary (e.g., via the platform 76 of the microdrive 56), by loosening the thumb screw 85, until the guide cannula tip 144 (see FIG. 6B) is located above the elongate opening 132 in the cinch tube 108. That is, the guide cannula 138 may be raised until the catheter 156 is visible within the elongate opening. In one embodiment, the guide cannula 138 will clear the elongate opening 132 when the head 140 of the guide cannula abuts the O-ring 172. The guide cannula 138 may then be locked at this new location relative to the fixed platform 74, e.g., with the thumb screw 85. With the guide cannula 138 retracted, the clinician may now optionally mark the catheter 156 at the cinch window 130 to ensure that catheter movement during subsequent procedures does not occur (alternatively or additionally, the catheter may be marked at an earlier time, e.g., at or near a surface of the dura 99).

Figure 10A:
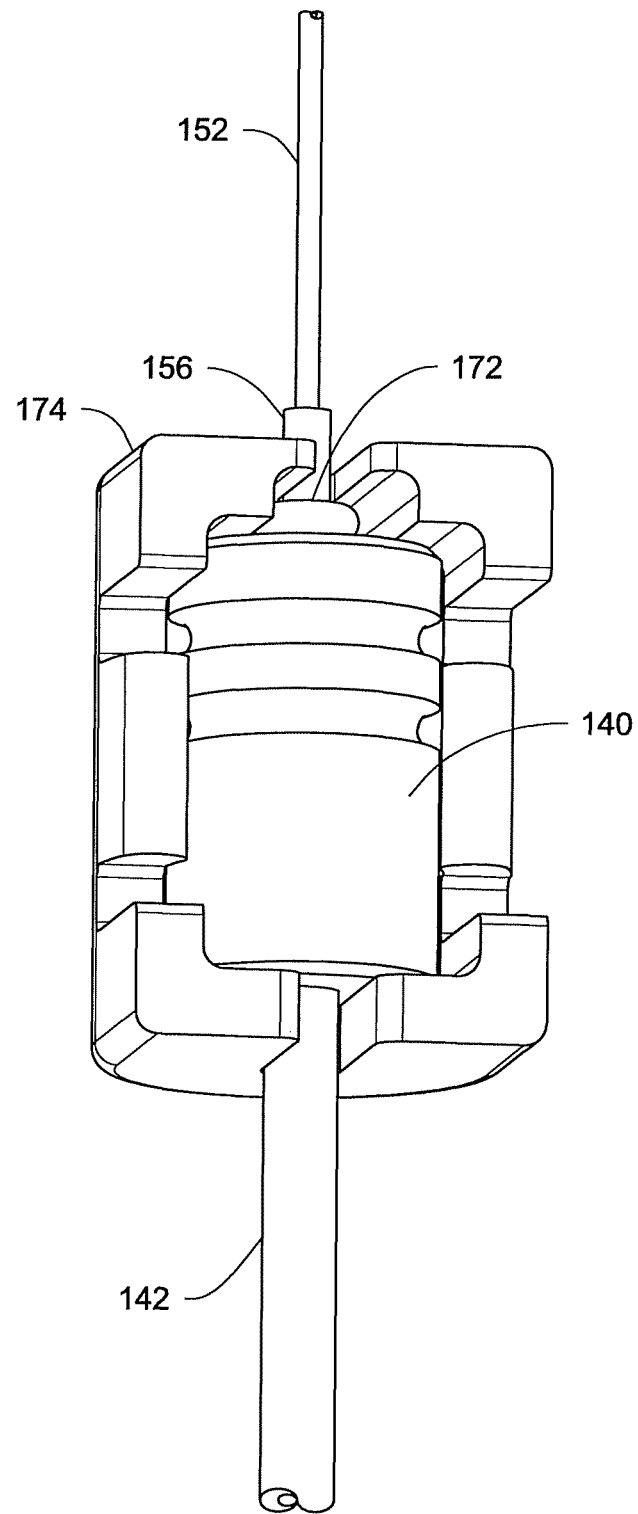
Figure 10B:
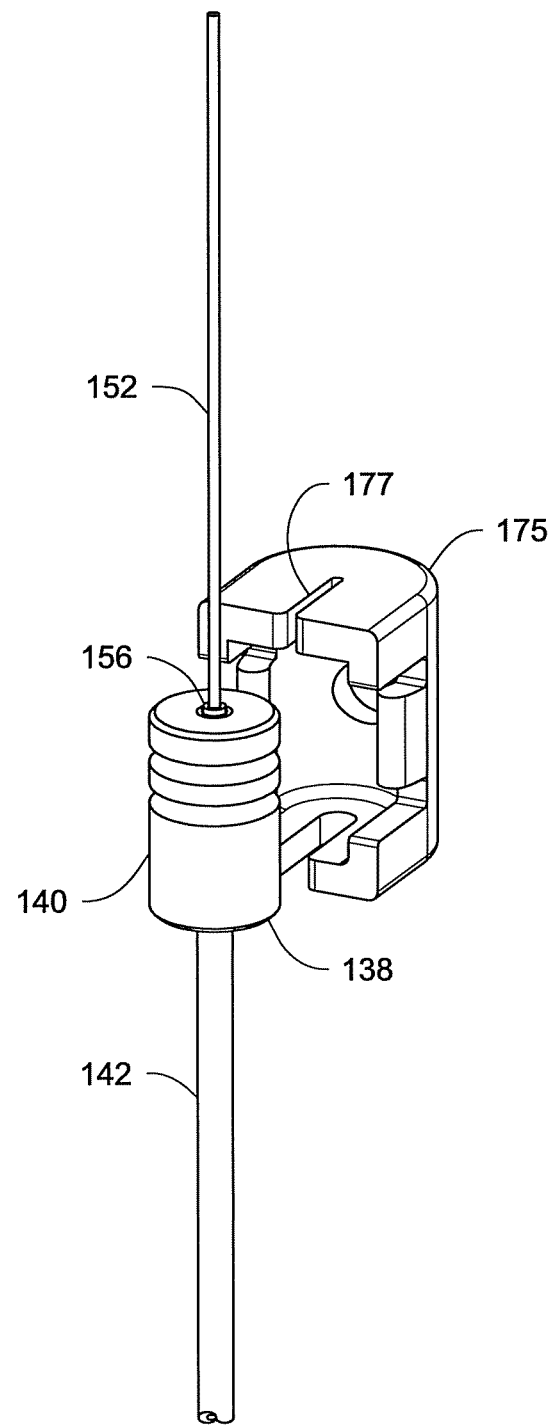

As shown in FIGS. 9 and 10A, with the guide cannula 138 retracted and secured, the catheter may be supported in place by the cinch tube 108 and guide tube 106. At this point, a removable retainer 174 may be side-loaded over the head 140 of the guide cannula and the O-ring 172. The retainer 174 may define one or more surfaces that receive and immobilize the O-ring 172 relative to the head 140, and via friction, secures the catheter 156 relative to the guide cannula (which is itself secured to the fixed platform 74 via the screw 85 (see also, e.g., FIG. 4)) during retraction of the stylet 152. Since it is side-loaded (e.g., attached from a direction transverse or lateral to the longitudinal axis of the guide cannula), the retainer 174 may be installed and removed without interference from other components in the system 100.

With the catheter 156 held fixed by the retainer 174, the stylet 152 may be retracted, e.g., moved in the direction 176 shown in FIG. 9, either manually or by the motorized carrier platform 76 (see, e.g., FIG. 3). To ensure that additional fluid volume created within the catheter 156 as a result of stylet extraction does not interfere with positive flow of the PBS fluid out the catheter tip, the extraction rate of the stylet and the infusion rate of the PBS fluid may be set accordingly. For instance, in one embodiment, the stylet may be retracted at a constant linear rate of approximately 18 min/min or less while infusing PBS fluid at a controlled volumetric flow rate of about 5 µl/min. However, most any combination of retraction and infusion rates that attempts to maintain positive catheter fluid flow is acceptable. The time it takes to retract the stylet sufficiently may depend on several factors, e.g., the skull-to-target distance 104 (see FIG. 4) and how far above the elongate opening 132 the clinician wants the tip 166 of the stylet (see FIG. 8) to be ultimately positioned. In one embodiment, the stylet is retracted until the tip is about 15 mm above the elongate opening 132. Once the stylet reaches the desired retracted position, the infusion flow may continue at the same or a lesser rate to maintain positive PBS fluid flow.

As stated elsewhere herein, other cannula systems in accordance with embodiments of the present invention may not require the use of infused PBS and, as a result, may not include the O-ring 172. In such an embodiment, a retaining member 175 such as that illustrated in FIG. 10B may be utilized. Like the retaining member 174, the retaining member 175 may be side-loaded over the head 140 of the guide cannula 138. It also defines a slot 177 that is sized to permit passage of the stylet 152, but is sufficiently narrow so as to restrict movement of the catheter 156. As a result, the stylet may be withdrawn without displacing the catheter 156, i.e., the catheter is at least longitudinally immobilized by the retainer during stylet extraction. Exemplary retaining members are described in more detail in U.S. patent application Ser. No. 13/247,203.

Figure 11:
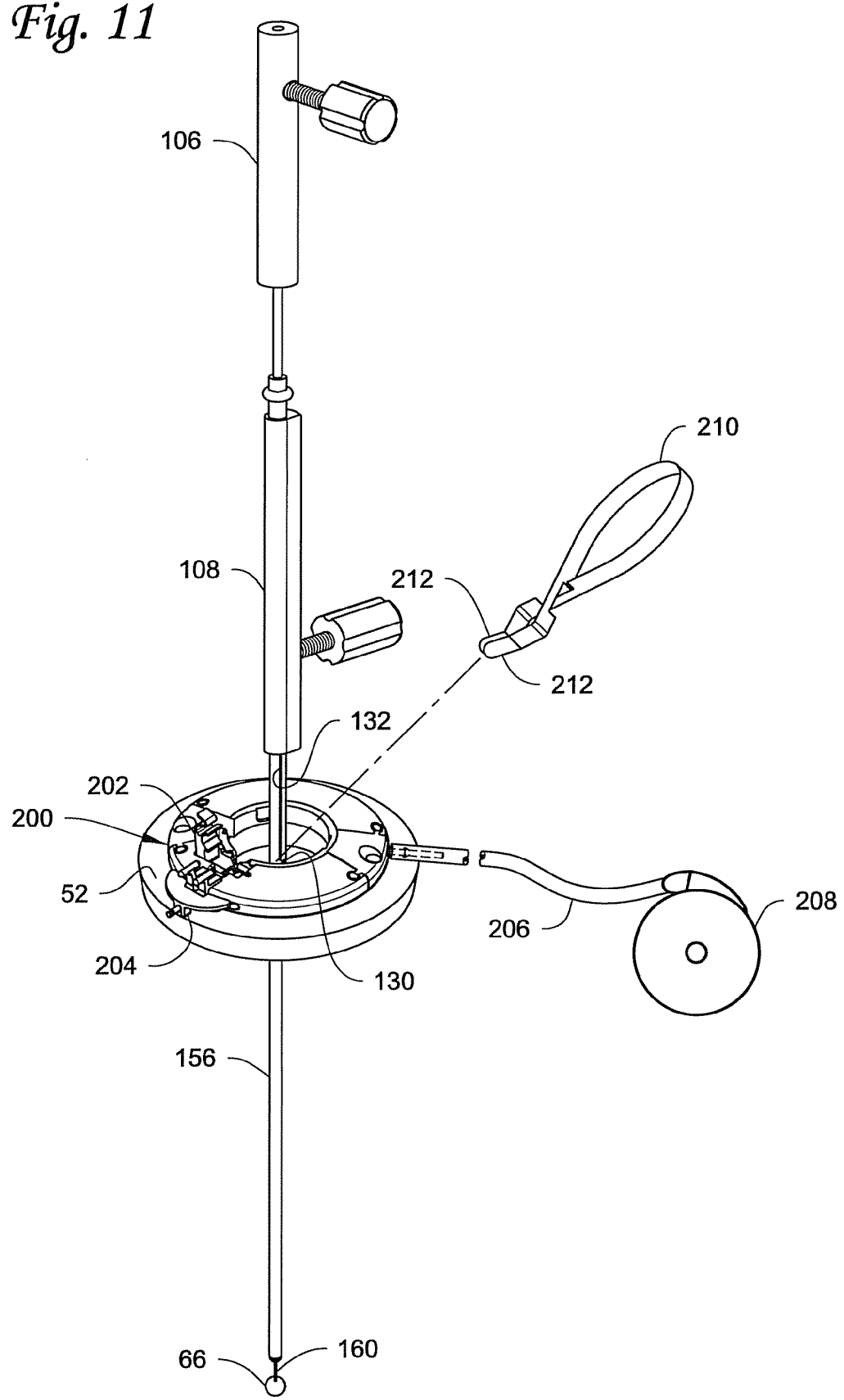
FIG. 11 is a perspective view of a portion of an exemplary cannula system during use showing a burr hole anchor attached to the skull around the burr hole, but before installation of a clamp or cinch member.
Figure 12:
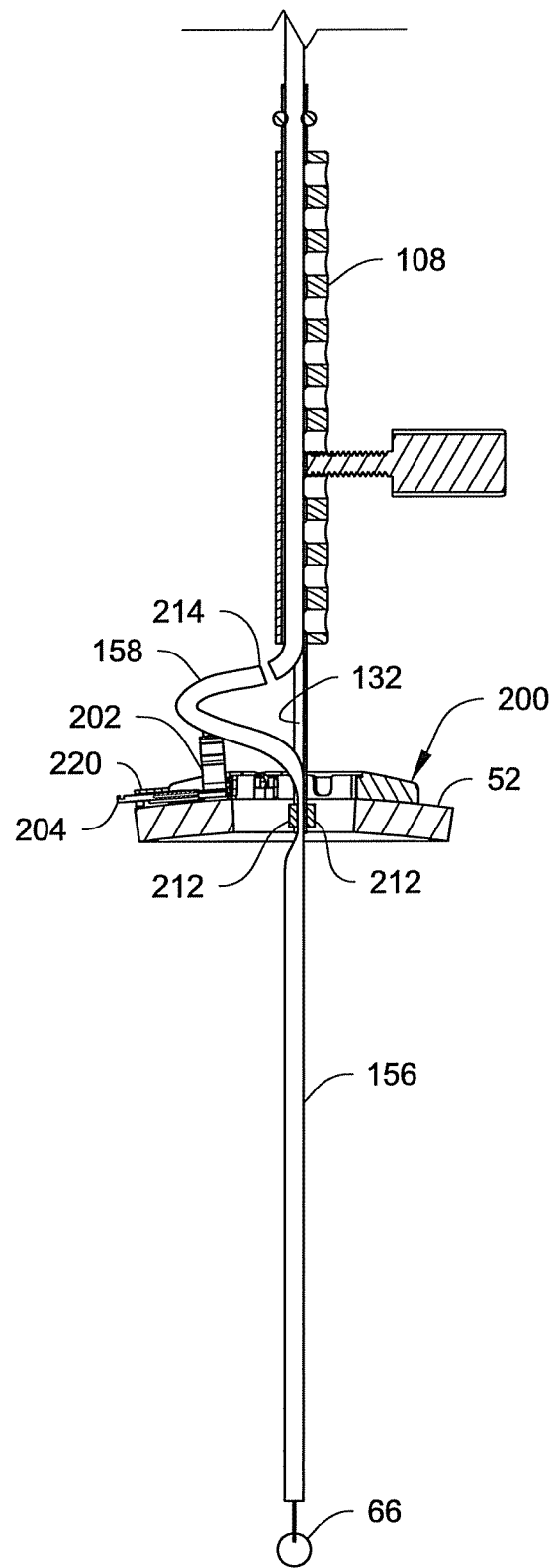
FIG. 12 is a section view of the system after the catheter is lowered (from above the cinch member), wherein it bows out of the cinch tube and is subsequently severed.

With reference now to FIGS. 11 and 12, the lower portion of the cinch tube 108 is shown relative to the burr hole anchor 200, which is now illustrated in more detail. Once again, the illustrated burr hole anchor 200 may be configured as described and illustrated in U.S. patent application Ser. No. 12/357,120. As a result, it may include a catheter cutting module 202 for cutting the therapy catheter 156 to the appropriate length, and a catheter connection module 204 for coupling the catheter 156 to a therapy source, e.g., to the implanted infusion pump 208 via the source catheter 206. Note that various elements, e.g., parts of the cannula system, may be excluded from these and the following views for clarity.

With the guide cannula 138 now retracted above the elongate opening 132 (and therefore not visible in FIGS. 11-12), a clamping or cinch member 210 may be attached to the cinch tube 108 such that one or more, e.g., first and second clamp elements 212 of the cinch member may engage the cinch tube at the cinch window 130 (see also FIG. 5A). In the illustrated embodiment, one of the opposing clamp elements 212 may enter the cinch tube 108 (i.e., pass through the window 130) and press the catheter body 158 firmly against the inner surface of the cinch tube to immobilize the device relative to the cinch tube (when the device is positioned within the cinch tube). At the same time, a second opposing clamp element 212 may press against the outer surface of the cinch tube opposite the cinch window 130. A body of the cinch member 210 may then lean or rest against an upper edge of the anchor 200 and thereby be supported by the anchor during the procedure. As a result, when the cinch member 210 is attached to the cinch tube 108, the first and second clamp elements 212 may effectively apply a clamping force configured to pinch the catheter against the cinch tube 108. Accordingly, the cinch member 210 may occlude the lumen of the catheter 156 while also immobilizing the catheter relative to the cinch tube 108 (and, thus, relative to the anchor 200) at the window 130. While illustrated herein as a separate clamping member, the cinch member 210 could be integrally formed with, or permanently or semi-permanently attached to (e.g., pinned, or welded), the cinch tube without departing from the scope of the invention.

Where utilized with an infusate flow, the stylet 152 may continue to infuse the catheter during attachment of the cinch member 210. And, although the cinch member 210 cuts off positive flow of PBS fluid through the catheter once attached, it may also entrap a column of the PBS fluid between the clamp elements 212 and the distal tip or end of the catheter 156. This "sealed" column of fluid may assist with the prevention of blood entry through the side flow openings 163 of the catheter.

While various cinch members or clamps may be utilized without departing from the scope of the invention, some embodiments may utilize a Schwartz Micro Serrefine vascular clamp such as model nos. 18052-02 or 18055-05 distributed by Fine Science Tools, Inc., of Foster City, Calif., USA. These cinch members may be compressed or pinched by the clinician to separate the clamp elements 212. Once the pinching force is released, the clamp elements are biased towards one another, thereby providing the desired clamping force. For clarity, the cinch member 210 may be illustrated diagrammatically or partially (or not shown at all) in the remaining views.

As indicated in FIG. 12, once the catheter 156 is clamped by the cinch member 210, the clinician may disconnect the stylet 152 (see FIG. 7) from the carrier platform 76 (if the microdrive 56 is used). The catheter 156 may then be pulled or otherwise displaced downwardly, e.g., via access through the elongate opening 132. To assist with catheter displacement, the O-ring 172 may first be removed (e.g., pushed upwardly) from the catheter. That is, the portion of the catheter extending between the proximal end and the cinch window 130 may be displaced while the remaining or implanted portion of the catheter remains immobilized. Since the catheter 156 is clamped at the cinch window 130 by the cinch member 210, downward movement of an upper portion of the catheter may cause the catheter to bow out of the elongate opening 132 above the cinch window 130 as shown. A blunt instrument may be used to initiate the bow if desired.

Once the catheter 156 is bowed, it may be severed by the clinician near the top of the bow, e.g., at or near a cut location 214 between the cinch location (window 130) and the proximal or upper end of the catheter, preferably near the upper end of the elongate opening 132. As an optional procedure, the severing process could be conducted with a heated cutting member (e.g., heated cautery forceps) that would cut and seal the now severed tips of the catheter. Alternatively, radio frequency energy could be used to cut and seal the catheter. Such a step may be advantageous to further ensure sealing of the catheter 156. However, this step is optional as, at least in some embodiments, the cinch member 210 may itself sufficiently seal the catheter.

Figure 13:
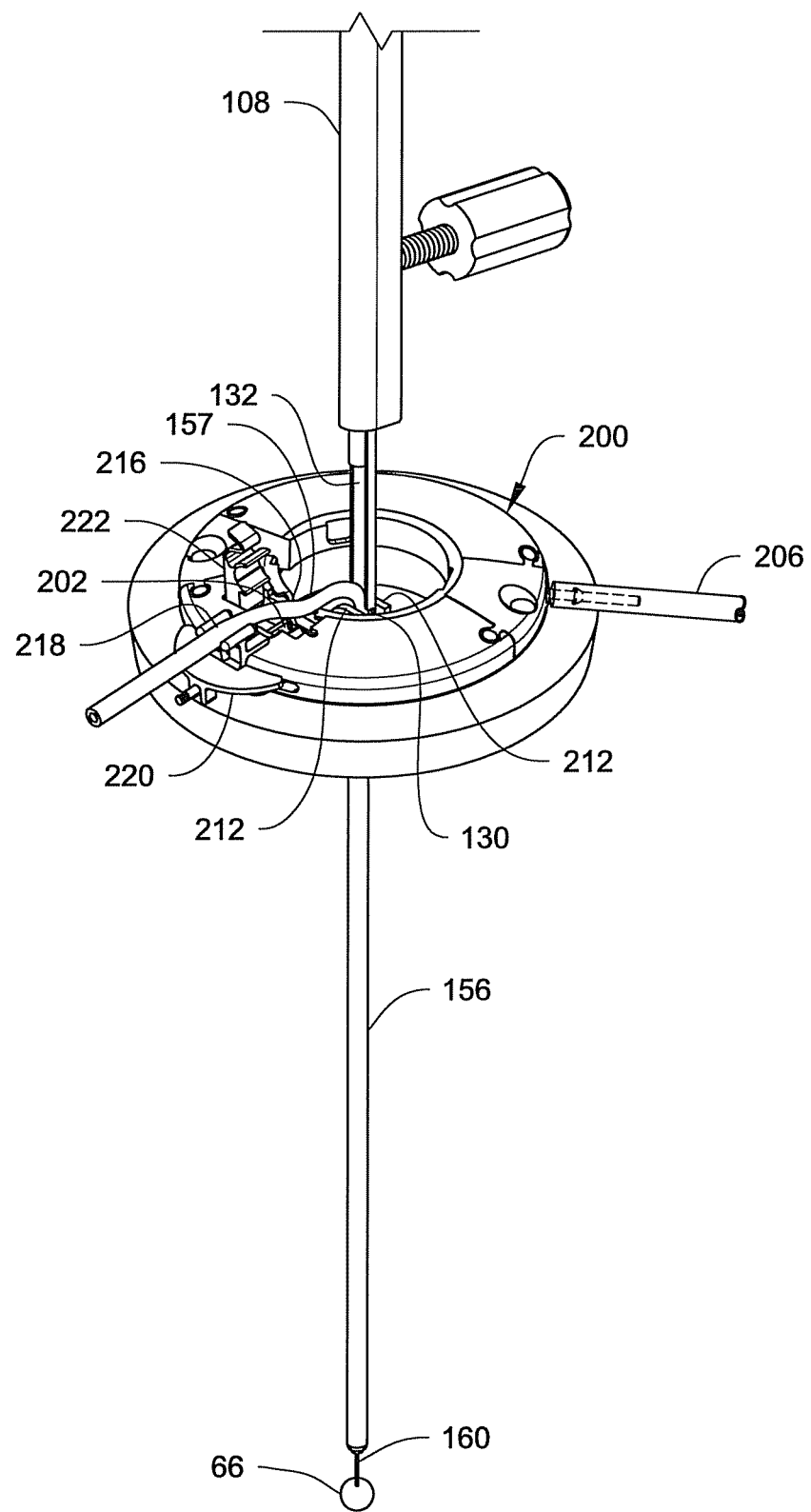
FIG. 13 illustrates a perspective view of the burr hole anchor and cinch tube after the severed catheter is placed into cinch points on the anchor and on a clip attached to the anchor, the cinch points configured to hold the catheter in a cutting position.
Figure 14:
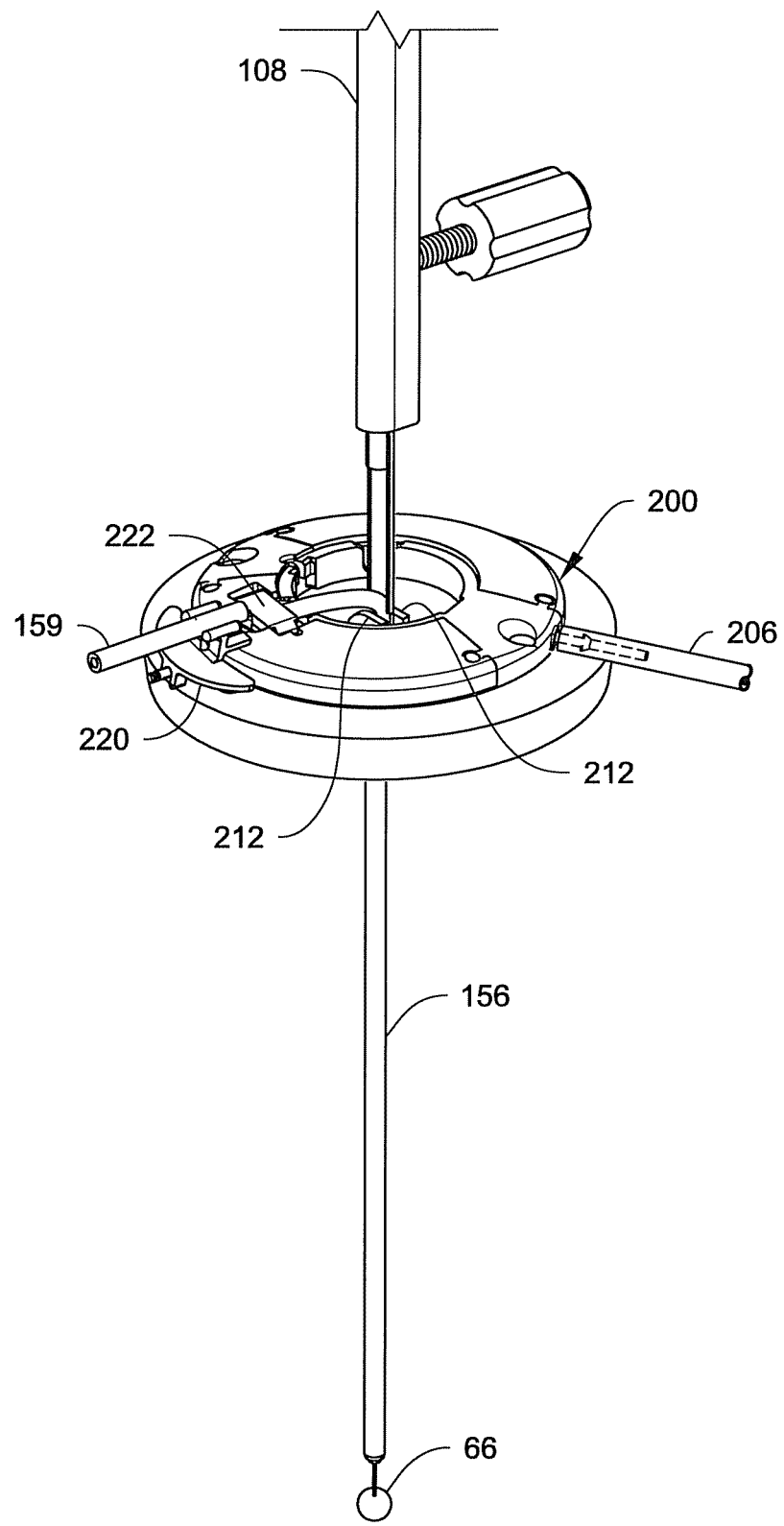
FIG. 14 is a perspective view of the burr hole anchor and cinch tube after the catheter has been cut by a cutting module of the anchor.
Figure 15:
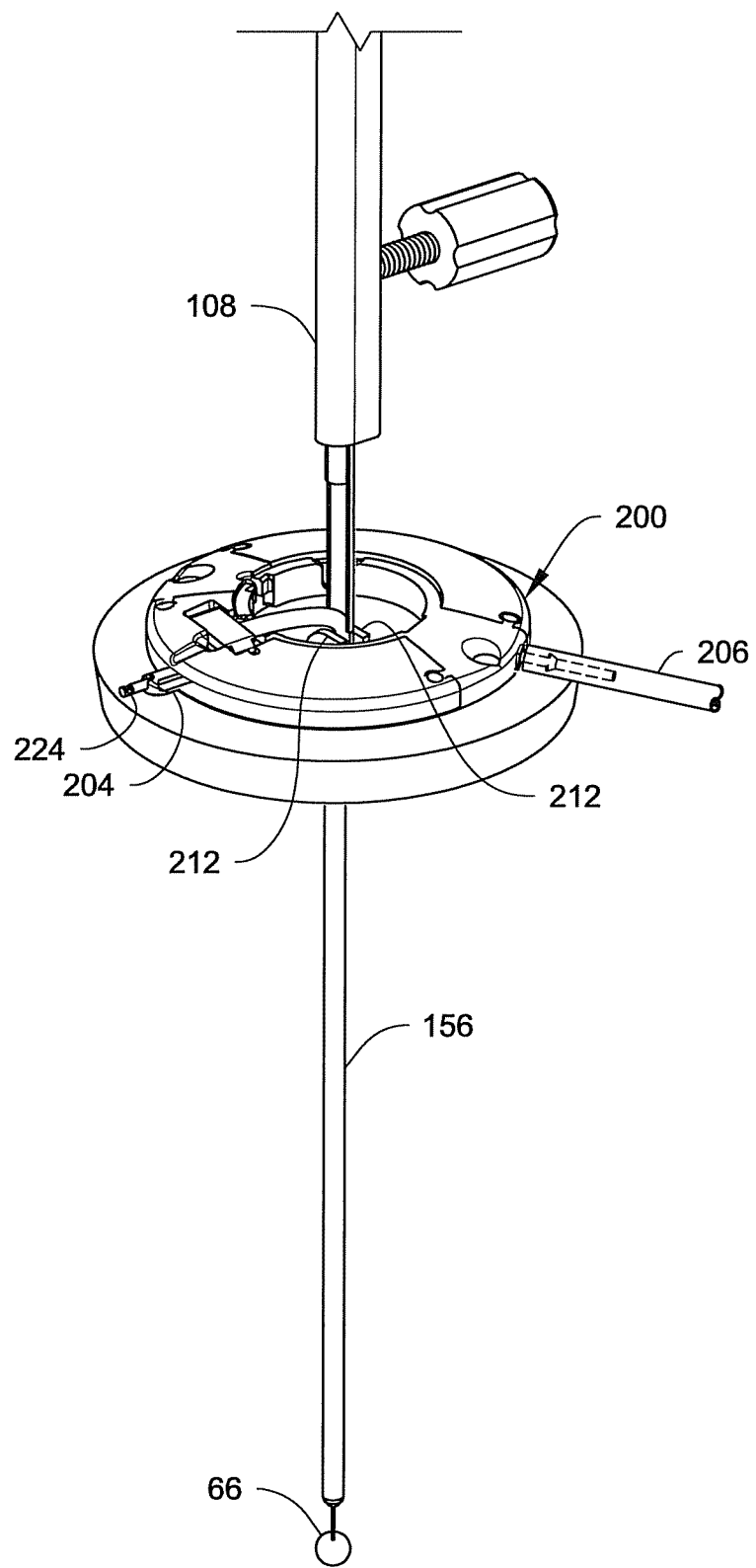
FIG. 15 illustrates the burr hole anchor and cinch tube after the catheter has been cut and the clip (with a cut segment of the catheter held therein) removed.
Figure 16A:
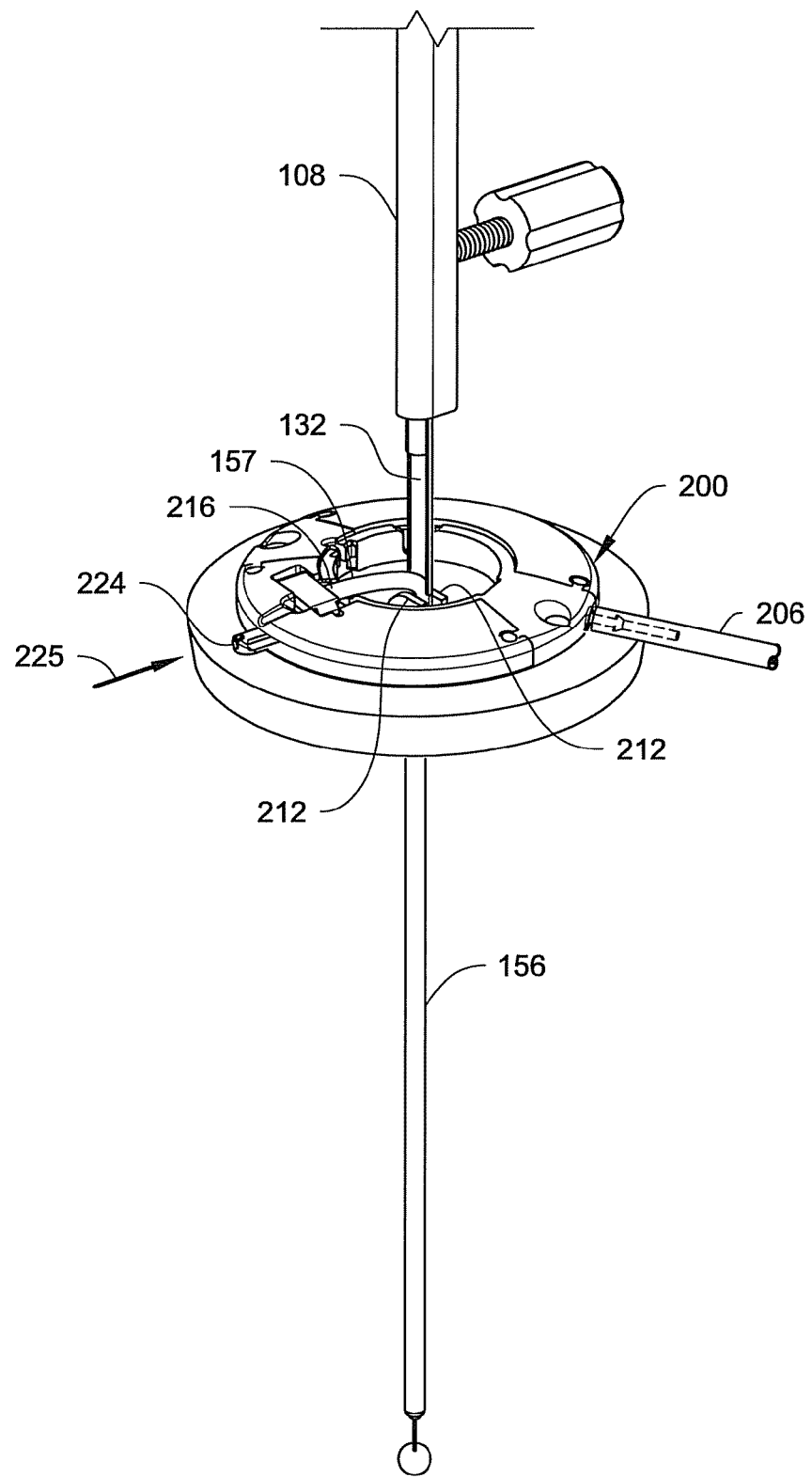
Figure 16B:
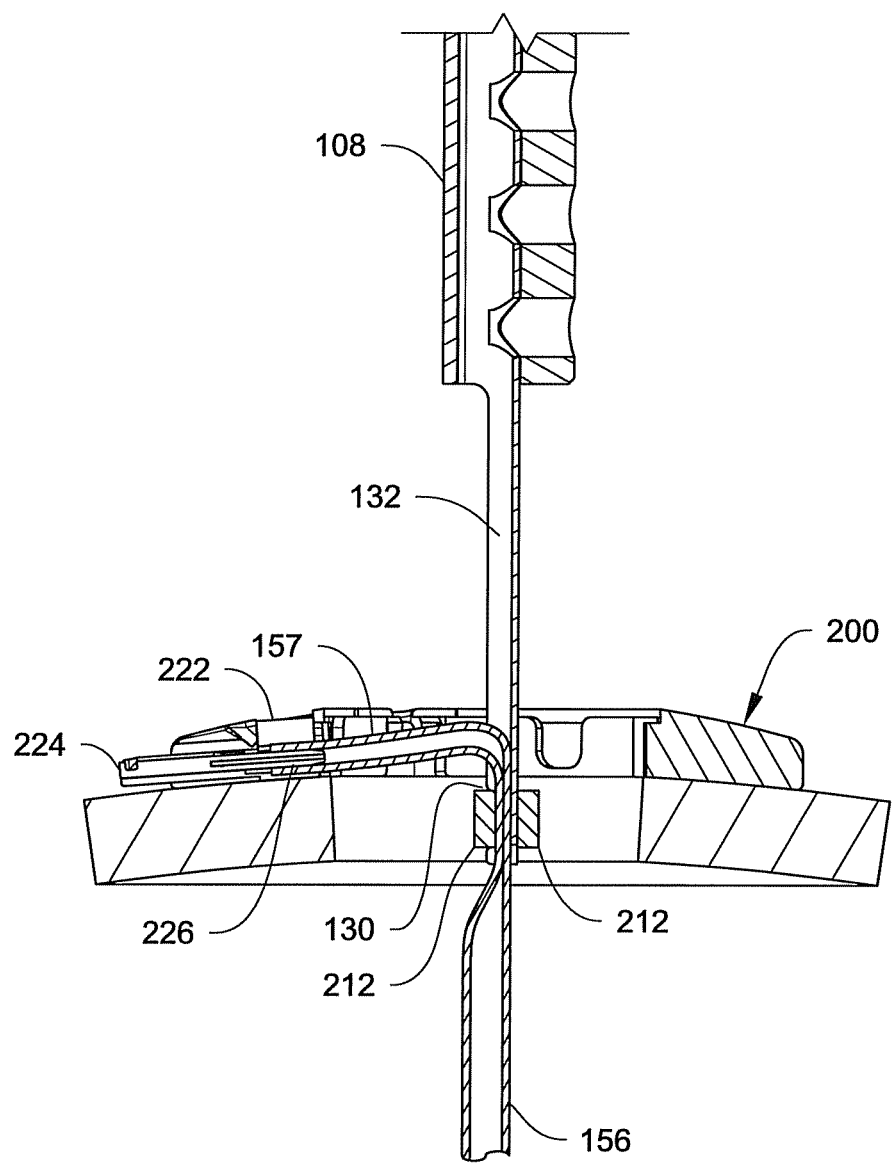

As shown in FIG. 13, a newly cut end segment 157 of the implanted catheter 156 may now be placed into a cinch point 216 located in a slot on a base of the anchor 200 and into a cinch point 218 formed on a removable clip 220 attached to the base (the elongate opening 132 and the cinch points having previously been aligned). With the end segment 157 of the catheter held in the cinch points, a cutting member of the cutting module 202 attached to the anchor (e.g., a door 222) may be moved from an open position shown in FIG. 13, to a closed position shown in FIG. 14. As the door 222 closes, it may cut the catheter end segment 157 to the desired length. An extraneous segment 159 of the catheter 156 is then retained within the clip 220 as shown in FIG. 14. The clip 220 (and the retained segment 159) may then be removed as indicated in FIG. 15.

With the clip 220 removed, a push pin 224 of the connection module 204 may be accessible to the clinician. The push pin 224 (see FIG. 15) may be pushed inwardly as indicated by the arrow 225 in FIG. 16A. In one embodiment, the catheter 156 may be held, e.g., with tweezers, at or near the first cinch point 216 as the push pin is moved. As the push pin is displaced, it drives a hollow delivery pin 226 (see FIG. 16B) slidably attached to the anchor into the immobilized end segment 157 of the catheter 156. The hollow pin 226 may, via various tubing conduits (not shown) contained within the anchor 200, be fluidly connected with the source catheter 206, which is itself connected to the infusion source (see e.g., FIGS. 11, 13, 14, 15, and 16A). As stated elsewhere herein, the source catheter 206 and anchor 200 (e.g., delivery pin 226) may be primed prior to actuation of the push pin 224. As a result, little air is introduced into the system during this process. U.S. patent application Ser. No. 12/357,120 describes an exemplary anchor similar to the anchor 200 in more detail.

If desired, the clinician may open the door 222 at this time to visually inspect the connection between the hollow pin 226 and the end segment 157 of the catheter 156. If the connection is satisfactory, the door may be re-closed. Otherwise, manual connection may be performed.

Figure 17:
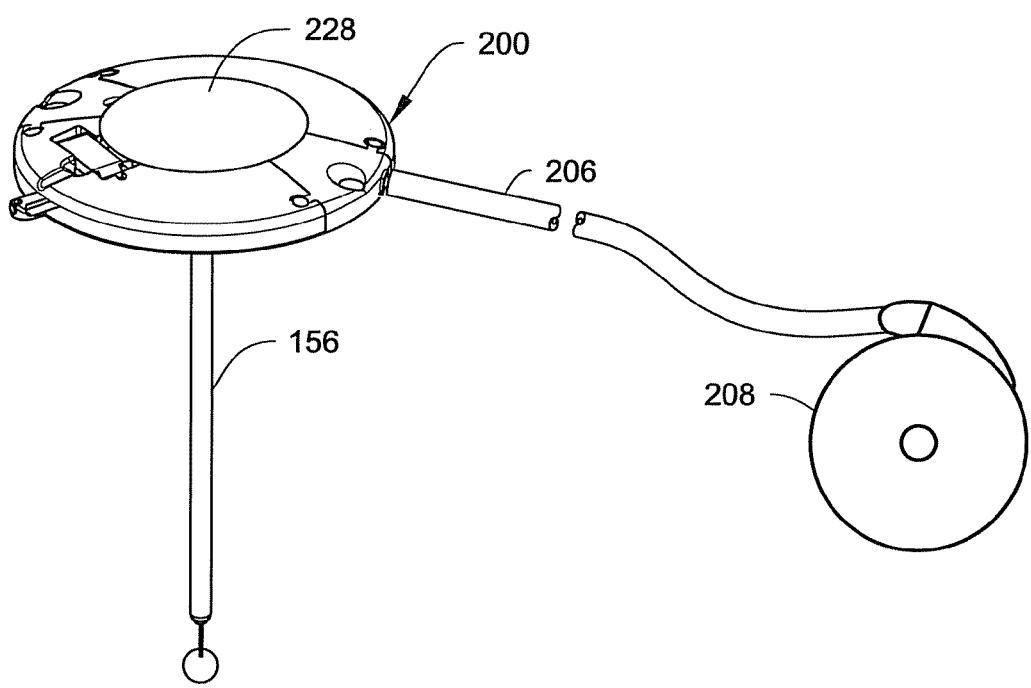
FIG. 17 is a perspective view after removal of the cinch tube, cinch member, and cannula system and installation of an anchor cap member.

At this point, the cinch member 210 may be removed and the cinching cannula 108 may be raised and removed from the stereotactic system. An optional cap 228 may be attached to the base 200 to cover the burr hole as shown in FIG. 17. Finally, any incision made to expose the burr hole may be closed (sutured).

Once the pin 226 is engaged with the catheter 156, the pump 208 may be activated and a bolus of therapeutic agent, e.g., 10 µl/min for 10 minutes, may be infused. Such a bolus delivery may prime the entire catheter length and furthermore assist with flushing out any blood that may have entered the needle tip during implantation. As one of skill may appreciate, bolus parameters may be adjusted to suit most any configuration. Thereafter, the pump may proceed to infuse the therapeutic substance in accordance with the desired therapy profile.

Systems and methods in accordance with embodiments of the invention as described above may allow immobilization of the catheter (after the tip is positioned) while the catheter is cut, anchored, and/or connected to the therapy source. As a result, inadvertent catheter movement may be minimized. Moreover, exemplary systems and methods of the present invention may reduce idle time (e.g., the time in which the catheter is not sealed or not connected to the pump such that blood may begin to flow into the catheter) from a typical 20-40 minutes to a matter of a few minutes or even seconds. In one instance using the push pin anchor described and illustrated herein, it is believed that the idle time may be reduced to about 10 seconds to about three minutes, less than the approximately 10 minutes or more typically needed for blood to clot within the catheter. With idle times in this range, blood entry into the catheter may be substantially reduced or even eliminated as compared to conventional approaches.

Cannula systems and methods in accordance with embodiments of the instant invention may also permit the sequential implantation of multiple catheters per burr hole by utilizing a burr hole anchor with multiple cutting and connection modules per anchor. As a result, multi-site delivery via a single burr hole may be achieved.

Illustrative embodiments of this invention are discussed and reference has been made to possible variations within the scope of this invention. These and other variations, combinations, and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A cannula system for immobilizing a tip of a catheter relative to a target site located within a mammalian skull while the catheter is being secured relative to a burr hole aligned with the target site, the system comprising:
   a guide tube comprising a body fixable relative to a surgical apparatus located outside of the burr hole, and an elongate tubular extension protruding from the body of the guide tube towards the target site;
   an elongate cinch tube comprising an inner surface and an outer surface, the inner surface configured to slidably receive the extension therein, wherein a cinch window is formed between the inner and outer surfaces near a distal end of the cinch tube;
   a catheter configured for insertion through both the guide tube and the cinch tube; and
   a cinch member comprising a first clamp element configured to pass through the cinch window and compress the catheter against the inner surface of the cinch tube.

2. The system of claim 1, wherein the cinch tube also comprises a tubular body and a tubular extension extending from the body of the cinch tube towards the target site, the cinch window being formed in the tubular extension of the cinch tube, and further wherein the cinch tube defines an elongate opening formed along a longitudinal section of the tubular extension of the cinch tube proximate the cinch window.

3. The system of claim 1, further comprising a friction member positioned between the guide tube and the cinch tube.

4. The system of claim 1, wherein the cinch tube comprises a body and a tubular protrusion extending from the body towards the guide tube, the tubular protrusion defining one or more windows passing through the tubular protrusion.

5. The system of claim 4, further comprising an O-ring surrounding the tubular protrusion and extending inwardly through the one or more windows of the tubular protrusion.

6. The system of claim 1, wherein the cinch member further comprises a second clamp element, the first and second clamp elements configured to pinch the catheter against a portion of the cinch tube.

7. The system of claim 1, further comprising a fastener configured to threadably engage the guide tube and selectively lock the cinch tube in a position relative to the guide tube.

8. The system of claim 7, wherein the cinch tube defines a plurality of threaded apertures each operable to receive the fastener.

* * * * *